US011118017B2

(12) United States Patent
Iakovlev et al.

(10) Patent No.: US 11,118,017 B2
(45) Date of Patent: Sep. 14, 2021

(54) PROCESS FOR THE PRODUCTION OF BIOPRODUCTS FROM LIGNOCELLULOSIC MATERIAL

(71) Applicant: AMERICAN PROCESS INTERNATIONAL LLC, Atlanta, GA (US)

(72) Inventors: Mikhail Iakovlev, Atlanta, GA (US); Theodora Retsina, Atlanta, GA (US); Adriaan van Heiningen, Orono, ME (US); Myrto Papaioannou, Athens (GR); Eleni Natsi, Athens (GR)

(73) Assignee: American Process International LLC, Atlanta, GA (US)

( * ) Notice: Subject to any disclaimer, the term of this patent is extended or adjusted under 35 U.S.C. 154(b) by 0 days.

(21) Appl. No.: 16/866,266

(22) Filed: May 4, 2020

(65) Prior Publication Data
US 2021/0139653 A1 May 13, 2021

Related U.S. Application Data

(60) Provisional application No. 62/934,601, filed on Nov. 13, 2019.

(51) Int. Cl.
*C08H 8/00* (2010.01)
*C08H 7/00* (2011.01)

(52) U.S. Cl.
CPC ............... *C08H 8/00* (2013.01); *C08H 6/00* (2013.01)

(58) Field of Classification Search
CPC .................................. C08H 8/00; C08H 6/00
See application file for complete search history.

(56) References Cited

U.S. PATENT DOCUMENTS

| | | | |
|---|---|---|---|
| 1,856,567 A | 5/1932 | Theodor et al. | |
| 2,060,068 A | 11/1936 | Groombridge et al. | |
| 3,523,060 A | 8/1970 | Herdle et al. | |
| 3,525,667 A | 8/1970 | Ingruber et al. | |
| 3,585,104 A | 6/1971 | Kleinert | |
| 4,100,016 A | 7/1978 | Diebold et al. | |
| 4,211,605 A | 7/1980 | Saxton et al. | |
| 4,764,596 A | 8/1988 | Lora et al. | |
| 7,754,457 B2 | 7/2010 | Foody et al. | |
| 8,003,352 B2 | 8/2011 | Foody et al. | |
| 8,030,039 B1 * | 10/2011 | Retsina .................. | C13K 13/00 435/161 |
| 8,038,842 B2 | 10/2011 | Retsina et al. | |
| 8,216,809 B2 | 7/2012 | Diner et al. | |
| 8,247,203 B2 | 8/2012 | Foody et al. | |
| 8,268,125 B2 | 9/2012 | Retsina et al. | |
| 8,304,213 B2 | 11/2012 | Diner et al. | |
| 8,585,863 B2 | 11/2013 | Retsina et al. | |
| 8,834,633 B2 | 9/2014 | Van Der Meulen et al. | |
| 8,864,941 B2 | 10/2014 | Retsina et al. | |
| 8,946,491 B2 | 2/2015 | Radtke et al. | |
| 8,980,599 B2 | 3/2015 | Tolan et al. | |
| 9,068,236 B2 | 6/2015 | Heikkila et al. | |
| 9,139,857 B2 | 9/2015 | Retsina et al. | |
| 9,193,982 B2 | 11/2015 | Sjoede et al. | |
| 9,322,072 B2 | 4/2016 | Retsina et al. | |
| 9,434,961 B2 | 9/2016 | Dottori et al. | |
| 9,453,249 B2 | 9/2016 | Retsina et al. | |
| 9,528,129 B2 | 12/2016 | Van Der Meulen et al. | |
| 9,574,212 B2 | 2/2017 | Foody et al. | |
| 9,624,436 B2 | 4/2017 | Hamilton et al. | |
| 9,631,057 B2 | 4/2017 | Realff et al. | |
| 9,631,316 B2 | 4/2017 | Retsina et al. | |
| 10,344,303 B2 | 7/2019 | Retsina et al. | |
| 10,421,667 B2 | 9/2019 | Foody et al. | |
| 2002/0192774 A1 | 12/2002 | Ahring et al. | |
| 2007/0254348 A1 | 11/2007 | Retsina et al. | |
| 2008/0293114 A1 | 11/2008 | Foody et al. | |
| 2010/0268000 A1 | 10/2010 | Parekh et al. | |
| 2011/0165643 A1 | 7/2011 | Retsina et al. | |
| 2011/0201084 A1 | 8/2011 | Wyman et al. | |
| 2011/0312033 A1 | 12/2011 | Gao et al. | |
| 2012/0202253 A1 | 8/2012 | Retsina et al. | |
| 2013/0071903 A1 | 3/2013 | Rowland et al. | |

(Continued)

FOREIGN PATENT DOCUMENTS

| | | |
|---|---|---|
| EP | 2376642 A2 | 10/2011 |
| EP | 2358890 B1 | 3/2013 |

(Continued)

OTHER PUBLICATIONS

Achyuthan et al., "Supramolecular Self-Assembled Chaos: Polyphenolic Lignin's Barrier to Cost-Effective Lignocellulosic Biofuels," Molecules, 15(12):8641-8688, Nov. 2010.
Aro et al., "Production and Application of Lignosulfonates and Sulfonated Lignin," ChemSusChemr., 10(9):1861-1877, Mar. 2017.
Aziz et al., "Organosolv Pulping—A Review," Tappi J (USA), 72(3):169-175, Mar. 1989.
Buzás et al., "Influence of pH on the Growth and Ethanol Production of Free and Immobilized *Saccharomyces cerevisiae* Cells," Biotechnol. Bioeng., 34:882-884, Sep. 1989.
Carvalheiro et al., "Hemicellulose Biorefineries: A Review on Biomass Pretreatments," J Scient Ind Res., 67(11):849-864, Nov. 2008.
Chen et al., "Pulp Characteristics and Mill Economics for a Conceptual So2-ethanol-Water Mill," AGRIS, 1990 Pulping Conference, pp. 663-672, 1992.

(Continued)

*Primary Examiner* — Pancham Bakshi
(74) *Attorney, Agent, or Firm* — Haukaas Fortius PLLC; Michael H. Haukaas

(57) ABSTRACT

A process for the production of ethoxylated and hydroxylated lignin fractions, cellulose, lignocellulosic sugars, and ethanol in high yields is provided. The process comprises steaming, pretreatment, chemical recovery, saccharification, and optionally fermentation. A combination of pretreatment conditions is provided resulting in simultaneously high yields of ethoxylated or hydroxylated lignin and cellulose or cellulosic sugars and hemicellulosic sugars. High yield production of ethanol through fermentation can be obtained using this process.

10 Claims, 5 Drawing Sheets

(56) References Cited

U.S. PATENT DOCUMENTS

| | | |
|---|---|---|
| 2013/0143289 A1 | 6/2013 | Meulen et al. |
| 2013/0274456 A1 | 10/2013 | Parekh et al. |
| 2014/0106426 A1 | 4/2014 | Retsina et al. |
| 2014/0154756 A1 | 6/2014 | Nelson et al. |
| 2014/0170713 A1 | 6/2014 | Retsina et al. |
| 2014/0186898 A1 | 7/2014 | Retsina et al. |
| 2014/0186899 A1 | 7/2014 | Retsina et al. |
| 2014/0186901 A1 | 7/2014 | Retsina et al. |
| 2015/0232703 A1 | 8/2015 | Nelson et al. |
| 2015/0246978 A1 | 9/2015 | Szczepanik |
| 2015/0354017 A1 | 12/2015 | Wang et al. |
| 2016/0060667 A1 | 3/2016 | Monclin et al. |
| 2016/0273163 A1 | 9/2016 | Gong et al. |
| 2016/0312249 A1 | 10/2016 | Foody et al. |
| 2017/0002387 A1 | 1/2017 | Retsina et al. |
| 2017/0183698 A1 | 6/2017 | Noordam et al. |
| 2017/0342443 A1 | 11/2017 | Smits |
| 2017/0369957 A1 | 12/2017 | Jansen et al. |
| 2018/0037863 A1* | 2/2018 | Foody ............ C12Y 302/01004 |
| 2018/0037915 A1 | 2/2018 | Foody et al. |
| 2018/0251941 A1 | 9/2018 | Nelson et al. |
| 2018/0355303 A1 | 12/2018 | Rowland et al. |
| 2018/0363017 A1 | 12/2018 | Tolan et al. |
| 2019/0106464 A1 | 4/2019 | Oeser et al. |
| 2019/0106718 A1 | 4/2019 | Foody et al. |
| 2019/0194697 A1 | 6/2019 | Dechman et al. |
| 2019/0376236 A1 | 12/2019 | Sixta et al. |
| 2020/0056213 A1 | 2/2020 | Retsina et al. |

FOREIGN PATENT DOCUMENTS

| | | | |
|---|---|---|---|
| EP | 2588664 B1 | 1/2017 | |
| WO | 2007146245 A2 | 12/2007 | |
| WO | 2011106879 A1 | 9/2011 | |
| WO | 2014099186 A1 | 6/2014 | |
| WO | 2014106220 A1 | 7/2014 | |
| WO | 2014106221 A1 | 7/2014 | |
| WO | WO 2014/106222 * | 7/2014 | ............... C08H 8/00 |
| WO | 2014203271 A3 | 2/2015 | |
| WO | 2015200584 A1 | 12/2015 | |
| WO | 2015200868 A1 | 12/2015 | |
| WO | 2016029069 A1 | 2/2016 | |
| WO | 2016144881 A1 | 9/2016 | |
| WO | 2019090413 A1 | 5/2019 | |
| WO | 2019090414 A1 | 5/2019 | |

OTHER PUBLICATIONS

Chum et al., "Pretreatment-Catalyst Effects and the Combined Severity Parameter," Appl Biochem Biotechnol., 24-25(1):1-14, Mar. 1990.

Del Rio et al., "The Effect of Varying Organosolv Pretreatment Chemicals on the Physicochemical Properties and Cellulolytic Hydrolysis of Mountain Pine Beetle-Killed Lodgepole Pine," Appl Biochem Biotechnol., 161(1-8):1-21, May 2010.

Eliashberg et al.," Wood Delignification with So2 Solutions Free from Bisulphite," Trudy Leningrad. Lesotekh. Akad.,1960, 11 pgs.

Ewanick et al., "Acid-Catalyzed Steam Pretreatment of Lodgepole Pine and Subsequent Enzymatic Hydrolysis and Fermentation to Ethanol," Biotechnol Bioeng., 98(4):737-746, Nov. 2007.

Fatehi et al., "Chap. 2: Extraction of Technical Lignins from Pulping Spent Liquors, Challenges and Opportunities," Production of Biofuels and Chemicals from Lignin, Springer, 1st ed., 2016 edition, pp. 35-54, Oct. 2016.

Fernando et al., "Lignin Recovery from Spent Liquors from Ethanol-Water Fractionation of Sugar Cane Bagasse," Cellulose Chem Technol., 44(9):311-318, Sep. 2010.

Galbe et al., "A Review of the Production of Ethanol From Softwood," Appl Microbiol Biotechnol., 59(6):618-628, Sep. 2002.

Gütsch et al., "Purification of Eucalyptus Globulus Water Prehydrolyzates Using the HiTAC Process (High-Temperature Adsorption on Activated Charcoal)," Holzforschung, 65(4):511-518, Apr. 2011.

Holtzapple et al., "The Effect of Organosolv Pretreatment on the Enzymatic Hydrolysis of Poplar," Biotechnol. Bioeng., 26:670-676, Jul. 1984.

Kleinert, "Organosolv Pulping with Aqueous Alcohol," Tappi J., 57(8):99-102, Aug. 1974.

Kumar et al. "The Lignin Present in Steam Pretreated Softwood Binds Enzymes and Limits Cellulose Accessibility," Bioresour Technol., 103(1):201-208, Jan. 2012.

Lan et al., "High Titer Ethanol Production From SPORL-Pretreated Lodgepole Pine by Simultaneous Enzymatic Saccharification and Combined Fermentation," Bioresour Technol., 127:291-297, Jan. 2013.

Larsson, et al., "The Generation of Fermentation Inhibitors During Dilute Acid Hydrolysis of Softwood," Enzyme Microb Tech., 24(3-4):151-159, Feb.-Mar. 1999.

Morales et al., "Effects of Residual Lignin and Heteropolysaccharides on the Bioconversion of Softwood Lignocellulose Nanofibrils Obtained by SO2-Ethanol-Water Fractionation," Bioresour Technol., 161:55-62, Jun. 2014.

Nakagame et al., "The Effect of Isolated Lignins, Obtained From a Range of Pretreated Lignocellulosic Substrates, on Enzymatic Hydrolysis," Biotechnol Bioeng., 105(5):871-879, Apr. 2010.

Nitsos et al., "Isolation and Characterization of Organosolvand Alkaline Lignins From Hardwood and Softwood Biomass," ACS Sustainable Chem. Eng., 4(10):5181-5193, Sep. 2016.

Olsson et al., "Fermentative Performance of Bacteria and Yeasts in Lignocellulose Hydrolysates," Process Biochem., 28(4):249-257, Jan. 1993.

Pan et al., "Biorefining of Softwoods Using Ethanol Organosolv Pulping: Preliminary Evaluation of Process Streams for Manufacture of Fuel-Grade Ethanol and Co-Products," Biotechnol Bioeng., 90(4):473-481, May 2005.

Pan et al., "Pretreatment of Lodgepole Pine Killed by Mountain Pine Beetle Using the Ethanol Organosolv Process: Fractionation and Process Optimization," Ind Eng Chem Res.,46(8):2609-2617, Mar. 2007.

Perez et al., "Effect of Process Variables on Liquid Hot Water Pretreatment of Wheat Straw for Bioconversion to Fuel-Ethanol in a Batch Reactor," J Chem Technol Biotechnol., 82(10):929-938 Oct. 2007.

Pfister et al., "The Formation of Monosaccharides and Aldonicand Uronic Acids During Sulphite Cooking," Paperi ja Puu (Paper and Wood), 59(11):711-720, 1977.

Primakov, "Delignification of Various Wood Species with So2 Aqueous-Alcohol Solutions," Proceedings of the All-Union Research and Development Institute of Pulp and Paper Industry, 47, 1961, 8pgs.

Primakov, "Larch Wood Delignification with So2 Aqueous-Alcohol Solutions," Proceedings of the All-Union Research and Development Institute of Pulp and Paper Industry, 46, 1961, 36pgs.

Primakov, "Optimization of Wood Pulping with So2 Aqueous-Alcohol Solutions," Wood Chemistry, 2:44-47, 1988.

Puumala, "Organosolv Pulping and a Preliminary Vapor-Liquid Equilibrium Study of a Sulfur Dioxide, Ethanol, Water System," A Thesis, Michigan Technological University, May 1991, pp. 1-67.

Pylkkänen, "Characterization of the Ethanol-So2 Pulping and a Preliminary Chemical Recovery Process Design," A Thesis, Lappeenranta-Lahti University of Technology LUT, Jun. 1992, pp. 1-141.

Rahikainen et al., Inhibition of Enzymatic Hydrolysis by Residual Lignins From Softwood—Study of Enzyme Binding and Inactivation on Lignin-Rich Surface, Biotechnol Bioeng., 108(12):2823-2834, Dec. 2011.

Saddler, et al., "Enzymatic Hydrolysis of Cellulose and Various Pretreated Wood Fractions," Biotechnol Bioeng., 24(6):1389-1402, Jun. 1982.

Sannigrahi et al., "Fundamentals of Biomass Pretreatment by Fractionation," 2013 JohnWiley & Sons, Ltd., pp. 201-222, Apr. 2013.

Schulze et al., "Advanced Process for Precipitation of Lignin From Ethanol Organosolv Spent Liquors," Bioresour Technol., 199:128-134, Jan. 2016.

Sixta, H., "Handbook of Pulp," Wiley-VCH, pp. 421.424, Mar. 2006.

(56) References Cited

OTHER PUBLICATIONS

Sjöström, "Wood Chemistry: Fundamentals and Applications," Academic Press; 2 edition, Chap. 7, Secs. 7.2-7.3, Jul. 1981.
Sklavounos et al., "Comparison of Two Conditioning Scheme S for Detoxifying SO 2 Ethanol Water Hydrolysate From Lignocellulosics for ABE Fermentation," Nord Pulp Pap Res J., 29(3):370-382, Mar. 2014.
Sklavounos et al., "Conditioning of SO2-Ethanol-Water Spent Liquor From Spruce for the Production of Chemicals by ABE Fermentation," Holzforschung, 65:551-558, Jun. 2011.
Sklavounos et al., "Oil Palm Empty Fruit Bunch to Biofuels and Chemicals via SO2-Ethanol-Water Fractionation and ABE Fermentation," Bioresource Technol., 147:102-109, Nov. 2013.
Sklavounos et al., "Study on Conditioning of SO2-Ethanol-Water Spent Liquor from Spruce Chips/Softwood Biomass for ABE Fermentation," Ind. Eng. Chem. Res., 52(11):4351-4359, Feb. 2013.
Söderström et al., "Effect of Washing on Yield in One- and Two-Step Steam Pretreatment of Softwood for Production of Ethanol," Biotechnol Prog., 20(3):744-749, May-Jun. 2004.
Stanciu et al., "Research Concerning Formation, Characterization and Recovery of Lignin Polymeric Deposits in order to Get Some Lignin-phenol-formaldehyde Resins," Materiale Plastice, 45(3):232-235, Sep. 2008.
Stenberg et al., "Optimisation of Steam Pretreatment of SO2-Impregnated Mixed Softwoods for Ethanol Production," J Chem Technol Biotechnol., 71:299-308, Jan. 1998.
Tian et al., "Comparisons of SPORL and Dilute Acid Pretreatments for Sugar and Ethanol Productions From Aspen," Biotechnol Prog., 27(2):419-427, Mar.-Apr. 2011.
Van Heiningen et al., "Reactions of Ethanol with Xylan and Lignin in Acid Catalyzed Organolv Pulping; Implications for Ethanol Recovery and Process Selection," 15th European Workshop on Lignocellulosics and Pulp, Jun. 2018, 4pgs.
Van Heiningen et al., "Reactions of Ethanol with Xylan and Lignin in Acid Catalyzed Organolv Pulping; Implications for Ethanol Recovery and Process Selection," Final Paper, 15th European Workshop on Lignocellulosics and Pulp, Jun. 2018, 4pgs.
Várnai et al., "Restriction of the Enzymatic Hydrolysis of Steam-Pretreated Spruce by Lignin and Hemicellulose," Enzyme Microb Tech., 46(3-4):185-193, Mar. 2010.
Wang et al., "Ethanol Production From Poplar Wood Through Enzymatic Saccharification and Fermentation by Dilute Acid and SPORL Pretreatments," Fuel, 95:606-614, May 2012.
Wells et al., "Rapid Sulfite Pulping in Concentrated Sulfur Dioxide Solutions," Tappi, 52(11): 2136-2140, Nov. 1969.
Westmoreland et al., "Sulfur Dioxide-Ethanol-Water Pulping of Hardwoods," Chem Eng Comm., 104:101-115, Jan. 1991.
Yamamoto et al., "The Effect of Chemical and Physical Characteristics of Spruce SEW Pulps on Enzymatic Hydrolysis," Cellulose, 21:3395-3407, Aug. 2014.
Yu et al., "The Effect of Delignification of Forest Biomass on Enzymatic Hydrolysis," Bioresour Technol., 102(19):9083-9089, Oct. 2011.
Zhou et al., "Bioconversion of Beetle-Killed Lodgepole Pine Using SPORL: Process Scale-up Design, Lignin Coproduct, and High Solids Fermentation without Detoxification," Ind. Eng. Chem. Res., 52(45):16057-16065, Oct. 2013.
Zhu et al., "Ethanol Production From SPORL-Pretreated Lodgepole Pine: Preliminary Evaluation of Mass Balance and Process Energy Efficiency," Appl Microbiol Biotechnol., 86(5):1355-1365, May 2010.
Zhu et al., "Using Sulfite Chemistry for Robust Bioconversion of Douglas-Fir Forest Residue to Bioethanol at High Titer and Lignosulfonate: A Pilot-Scale Evaluation," Bioresour Technol., 179:390-397, Mar. 2015.
Extended Search Report of the European Patent Office dated Oct. 7, 2020 in EP Application No. 20174836.5; 10pgs.
Yamamoto et al., "Total Mass Balances of SO2-ethanol-water (SEW) Fractionation of Forest Biomass," Holzforschung, 65:559-565, Jun. 2011.

\* cited by examiner

PROCESS FOR THE PRODUCTION OF BIOPRODUCTS FROM LIGNOCELLULOSIC MATERIAL

RELATED APPLICATIONS

This application claims priority under 35 U.S.C. § 119(e) to U.S. Provisional Patent Application No. 62/934,601 filed Nov. 13, 2019, which is incorporated herein by reference.

FIELD OF THE INVENTION

The present invention generally relates to pretreatment processes for converting lignocellulosic biomass to lignin, cellulose, and fermentable sugars.

BACKGROUND OF THE INVENTION

Commercial sulfite and Kraft pulping processes, having been practiced since the end of 19$^{th}$/beginning of 20$^{th}$ century, focus on production of cellulose from wood. The Kraft process uses sodium hydroxide and sodium sulfide at temperatures higher than 140° C., and sulfite process uses sulfur dioxide ($SO_2$) and salts of sulfurous acid, both sulfites and hydrogen sulfites, at temperatures of about 125-160° C. (Sjöström, 1981). Magnesium, calcium, sodium, and ammonium are used as bases. These processes suffer from substantial losses of valuable non-cellulose components, primarily lignin and hemicelluloses. The alkaline chemistry of the Kraft process substantially alters the lignin structure, while hemicellulosic sugars mostly degrade to hydroxy carboxylic acids, which are hard to recover. Sulfite processes utilize hydrogen sulfite anions among other chemical species, which results in lignin sulfonation to lignosulfonic acids and sugar oxidation to aldonic acids. Lignin is substantially altered by condensation and sulfur incorporation between lignin units in the Kraft process and by formation of sulfonic acids in sulfite processes. Substantial portions of the sugars of the lignocellulosic biomass are lost in both processes (>70% in Kraft, >20% in sulfite).

Both processes also have rather inefficient and/or expensive chemical recovery systems. In addition, a common variety of the sulfite process, namely the acid sulfite process, is very sensitive to raw material selection and particles size and shape. Many types of woody biomass including pine are not suitable for the acid sulfite process. Moreover, a long impregnation phase at low temperature is required in the sulfite process for the efficient transport of chemicals into the cell wall structure.

Organosolv processes were introduced in the 1930s (see, for example, the first patent by Kleinert and Tayenthal, U.S. Pat. No. 1,856,567, issued on May 3, 1932). In the organosolv process, lignocellulosic biomass is treated with an organic solvent and water in various ratios with or without the presence of catalyst, typically at temperatures of 160-210° C. The advantage of organosolv processes is that the presence of an organic solvent promotes dissolution of non-condensed lignin, which is said to be in near-native form, although the lignin becomes ethoxylated to an extent when ethanol is used as solvent. The most common organic solvents are alcohols, ketones, esters, organic acids, while the most common catalyst is sulfuric acid. The combination of high temperature and acidity in the organosolv process results in high sugar degradation, especially in uncatalyzed organosolv processes, where approximately 30% sugar loss is observed (van Heiningen et al., 2018).

Another disadvantage of organosolv processes is the limited delignification and limited removal of hemicelluloses from cellulose. Uncatalyzed organosolv processing of softwoods results in a high residual lignin content of the fibers. For example, Aziz and Sarkanen, 1989, report that uncatalyzed softwood organosolv pulps have a high residual lignin content (kappa number 80-100). After uncatalyzed organosolv pulping at 185° C. for 60 minutes, Kleinert (1974) obtained cellulosic pulp from spruce with about 5% residual lignin and 8% residual hemicelluloses at liquor-to-solid ratio of 10, which shows inefficient removal of hemicelluloses from softwoods, even at the very high liquor-to-solid ratio. At lower liquor-to-solid ratio, the delignification is considerably impaired.

The presence of catalysts increases the organosolv pretreatment efficiency, but it is still a challenge to produce pure cellulosic pulps. For example, mixed softwoods consisting of spruce, pine, and Douglas fir from lumber mill Whitewood residues pretreated in 60% ethanol with sulfuric acid as a catalyst (185-198° C. for 30-60 minutes, pH 2.0-3.4; liquor-to-solid ratio 7-10 kg/kg) produced cellulosic pulps with residual lignin content varying from 6.4 to 27.4% (Pan et al. 2005). Residual organosolv lignin, especially in non-sulfonated form, is known to decrease enzymatic digestibility by increasing non-productive enzyme adsorption on lignin (Nakagame et al., 2010, del Rio et al., 2011).

Organosolv lignin yields were reported at about 54-196 bone dry (BD) kg per BD metric tonne of wood (Sannigrahi and Ragauskas, 2013). The maximum lignin yield achieved by Nitsos et al., 2016, for catalyzed organosolv pulping was 62% for spruce and 69% for birch (based on original lignin content in feedstock). In another work, catalyzed organosolv pretreatment (Pan et al., 2007) achieved lignin yield of 78% but was characterized by 25% cellulose loss and 50% hemicellulose loss with high formation of furfural, hydroxymethylfurfural, and levulinic acid (65% ethanol, 1.1% sulfuric acid, 170° C., 60 min). Sulfuric acid catalyzed organosolv fractionation of sugarcane bagasse (150-160° C.) produced precipitated lignin at yields of 45-48% (Fernando et al., 2010).

For uncatalyzed organosolv processes where solvents are volatile alcohols, ketones, esters or other volatile compounds, the solvent in the spent pulping liquor can readily be recovered by distillation. However, alcohol chemically bound to lignin and sugars in organosolv processes is difficult to recover without addition of an acidic catalyst, which likely explains the high ethanol losses in the ethanol-based Alcell process.

Sulfur dioxide catalyzed organosolv processes utilizing $SO_2$ concentrations lower than about 3-6% have been reported. In these processes, a large portion of the sulfur dioxide reacts with lignin to form lignosulfonic acid, which is a strong acid with a pKa of about 1. The process is therefore similar in performance to sulfuric acid-catalyzed organosolv processes, with inefficient delignification and high sugar losses. According to Chum et al., 1990, sulfur dioxide catalyzed organosolv pretreatment of aspen at various conditions and a sulfur dioxide concentration of 0.2-1.7% produced pulps with residual lignin content of 6-15%. Pylkkanen, 1992, reported residual lignin content in cellulosic pulp of 3.7% and a very high residual hemicellulose content of 27.3% for $SO_2$ catalyzed organosolv pretreatment of black spruce at 3.5% $SO_2$, 55% ethanol, and 150° C. for 110 min. The residual lignin and hemicellulose content decreased to 1.4% and 6.5% at 180 min of pretreatment, respectively. The extent of sugar degradation at the relatively long treatment time (110-180 min) was not reported.

Del Rio et al., 2010, reported a residual lignin content in cellulosic pulp of 18.6% for $SO_2$ catalyzed organosolv pretreatment of Beetle-Killed Lodgepole Pine at 1.1% $SO_2$, 65% ethanol, and 170° C. for 60 min.

The AVAP® process (U.S. Pat. Nos. 8,038,842 and 8,268,125, both to Retsina et al.) utilizes sulfur dioxide, alcohol and water at $SO_2$ concentrations over 9%. It allows for efficient delignification and low sugar losses but employs high $SO_2$ concentrations, typically 12-15% in solution, translating into 36-60% on BD biomass. This requires handling and recycling of large quantities of sulfur dioxide. The yields of non-condensed lignin precipitated by removal of ethanol from the AVAP® spent liquors were reported in a number of publications and range from 37-54% of the original lignin in spruce, softwood logging residues, and Oil Palm Empty Fruit Bunches (Sklavounos et al., 2011, 2013a, 2013b, 2014), i.e. up to a maximum of about 150 BD kg per BD tonne softwood.

Enzymatic digestibility of cellulose is a key factor for an economic process. It is common knowledge that enzymatic digestibility of cellulose is most efficient when the cellulose purity is high, i.e., the cellulose contains only small amounts of residual hemicelluloses and lignin. It is well known in sulfite pulping that, in order to obtain efficient delignification (i.e. removal of lignin from cellulose) in the absence of base (calcium, magnesium, sodium or ammonium), sulfur dioxide concentration in the solution ought to be at about 12% or higher (so-called Kaufmann diagram, Kaufmann, 1951). At lower sulfur dioxide concentrations, a so-called "black cook" is observed, i.e., cellulose is heavily contaminated with condensed lignin. Accordingly, high sulfur dioxide concentrations are used in AVAP® process.

It is also a conventional knowledge that fiber explosion (e.g., rapid decrease in pressure leading to instantaneous evaporation of liquid within the fiber structure) after pretreatment results in increased enzymatic digestibility of cellulose, presumably due to disruption of the fiber cell wall structure providing improved enzyme accessibility to the cellulose surface, after the explosive decompression.

These current processes thus do not provide simultaneous high-yield production of non-condensed reactive lignin (higher than about 65% based on lignin in biomass or, for softwoods, higher than 180 BD kg lignin per BD metric tonne biomass) and fermentable monomeric sugars (higher than about 80% based on available polysaccharides in biomass or, for softwoods, higher than 585 BD kg per BD metric tonne biomass) in an economical manner. Furthermore, acidic pretreatment processes, for example, those utilizing sulfuric acid as catalyst, often suffer from creation of lignin sticky precipitates that clog the processing equipment resulting in increased downtime. Accordingly, there is a need for improved processes for converting lignocellulosic biomass to non-condensed lignin fractions, lignocellulosic sugars, and ethanol, in high yields, without the production of lignin sticky precipitates that clog the processing equipment.

SUMMARY

The present disclosure provides a process for lignocellulosic biomass valorization resulting in simultaneous production of non-condensed reactive lignin at over 75% based on original lignin amount in biomass and over 90% of available saccharides converted to monosaccharides. The process involves pretreatment with a solution of ethanol containing sulfur dioxide at moderate concentrations (6-8%), followed by recovery of chemicals, optional separation of non-condensed lignin, cellulose and hemicellulose saccharification, and optional fermentation of sugars to ethanol. The innovative combination of process steps combined as described herein thus provides significantly increased yields of both sugars and non-condensed lignin from lignocellulosic biomass and significantly decreased enzyme charge requirements. As a result of these improvements, a highly efficient and economical bioethanol production process has been achieved.

Accordingly, this disclosure provides a process for the production of ethoxylated and hydroxylated lignin fractions, cellulose, lignocellulosic sugars, and ethanol, in high yields, comprising:

(a) contacting lignocellulosic biomass in a first container with steam to provide steamed lignocellulosic biomass, wherein the lignocellulosic biomass absorbs water from the steam, removing air and optionally turpentine and/or other extractives from the lignocellulosic biomass; and transferring the steamed lignocellulosic biomass from the first container to a second container;

(b) contacting the steamed lignocellulosic biomass in a second container with a pretreatment liquor at a temperature between 145° C. and 165° C. under pressure for 20-120 minutes;

wherein the pretreatment liquor comprises 6-8 weight % sulfur dioxide, 30-60 weight % ethanol, and 32-64 weight % water (including water from the steamed lignocellulosic biomass), and the ratio of pretreatment liquor to lignocellulosic biomass, based on dry weight of the lignocellulosic biomass, is about 2.5 to 4.5 kg/kg (including water from the steamed lignocellulosic biomass in the mass of the pretreatment liquor);

thereby releasing and/or dissolving lignin and hemicellulose from the lignocellulosic biomass into the pretreatment liquor, resulting in a mixture comprising lignin and hemicellulose dissolved in the pretreatment liquor and a solid fraction comprising mainly cellulose (e.g., greater than about 85%, greater than about 90%, or greater than about 92%, cellulose in the solid fraction) from the lignocellulosic biomass, which mixture is referred to as the pretreated material;

wherein about 10-40% of the lignin from the lignocellulosic biomass is sulfonated to produce lignosulfonic acid (LS), at least 10% of the lignin moieties are ethoxylated, at least about 30% of the sugar moieties of the hemicellulose from the lignocellulosic biomass are hydrolyzed to monosaccharide form, and 20-70% of the sugar moieties of the hemicellulose from the lignocellulosic biomass are converted to ethyl glycosides (also referred to as ethoxylated sugars or sugar ethoxylates);

(c) releasing pressure from the second container, or from the pretreated material, for example, in a blow tank when in continuous mode operation, and recovering sulfur dioxide, and optionally ethanol, from gas released from the pretreated material as a result of releasing pressure;

(d) washing the solid fraction comprising mainly cellulose obtained from the second container with a solution comprising water and ethanol (ranging from about 0% to about 100% in ethanol concentration, e.g., about 0.1% to about 99.9% ethanol, typically about 50% ethanol), and further washing the solid fraction with water, to provide washed cellulose and a wash filtrate, thereby removing ethanol and dissolved material from the cellulose, wherein the wash filtrate contains the dissolved material, which comprises lignin, ethoxylated lignin, lignosulfonic acid (LS), hemicellulose oligomers, ethyl glycosides (or ethoxylated sugars), and monosaccharides;

(e) recovering ethanol from the wash filtrate by steam stripping, evaporation, successive flash stages, or by other methods, thereby precipitating lignin and ethoxylated lignin fractions, and optionally removing the precipitated lignin and ethoxylated lignin fractions;

(f) heating the material obtained after step (e) (i.e., the water, the lignin, ethoxylated lignin, lignosulfonic acid (LS), hemicellulose oligomers, ethyl glycosides (or ethoxylated sugars), and monosaccharides after removal of ethanol, optionally with the lignin and ethoxylated lignin fractions removed) at a temperature between 90° C. and 120° C. for 0.5-8 hours to hydrolyze the ethyl glycosides (or ethoxylated sugars) and hemicellulose oligomers to monosaccharides and to optionally hydrolyze ethoxylated lignin to release ethanol, to provide a composition, referred to as a hemicellulose stream, comprising of lignosulfonic acid and monosaccharides, and optionally lignin and hydroxylated lignin, wherein the lignin and hydroxylated lignin may optionally be removed;

(g) adjusting the pH of the washed cellulose stream from step (d) and contacting it with a cellulase, a glucosidase, a hemicellulase, or a combination thereof, to produce glucose and release a small amount of other sugars and insoluble lignin (referred to as the glucose fraction); or optionally combining the washed cellulose with the hemicellulose stream from step (f), adjusting the pH of the mixture and contacting it with a cellulase, a glucosidase, a hemicellulase, or a combination thereof, to produce glucose and hemicellulose sugars, and to release a small amount of insoluble lignin (where 'a small amount of insoluble lignin' refers to less than about 4%, less than about 5%, less than about 6%, or less than 10%, by weight, of washed cellulose fraction, in addition to any insoluble lignin in step (f));

(h) optionally combining the glucose fraction of step (g) with the hemicellulose stream of step (f) (comprising lignosulfonic acid, monosaccharides, and optionally lignin), to provide a fermentable composition;

or optionally utilizing the glucose fraction of step (g) and the hemicellulose stream of step (f) separately for further downstream pH adjustment and utilization (e.g., fermentation); and (i) optionally neutralizing any of the above separate or combined fractions and/or streams to appropriate pH level and subjecting them to fermentation to produce ethanol.

The disclosure also provides a process for the production of an ethoxylated lignin fraction, cellulose, lignocellulosic sugars, and ethanol, in high yields, comprising:

(a) contacting lignocellulosic biomass in a first container with steam to provide steamed lignocellulosic biomass, wherein the lignocellulosic biomass absorbs water from the steam, removing air and optionally turpentine and/or other extractives from the lignocellulosic biomass; and transferring the steam-treated lignocellulosic biomass from the first container to a second container;

(b) contacting the steamed lignocellulosic biomass in the second container with a pretreatment liquor at a temperature between 145° C. and 165° C. under pressure for 20-120 minutes;

wherein the pretreatment liquor comprises 6-8 weight % sulfur dioxide, 30-60 weight % ethanol, and 32-64 weight % water (including water from the steamed lignocellulosic biomass), and the ratio of pretreatment liquor to lignocellulosic biomass, based on dry weight of the lignocellulosic biomass, is about 2.5 to 4.5 kg/kg (including water from the steamed lignocellulosic biomass in the mass of the pretreatment liquor);

thereby releasing and/or dissolving lignin and hemicellulose from the lignocellulosic biomass into the pretreatment liquor, resulting in a mixture comprising lignin and hemicellulose dissolved in the pretreatment liquor and a solid fraction comprising mainly cellulose (e.g., greater than about 85%, greater than about 90%, or greater than about 92%, cellulose in the solid fraction) from the lignocellulosic biomass, which mixture is referred to as the pretreated material;

wherein about 10-40% of the lignin from the lignocellulosic biomass is sulfonated to produce lignosulfonic acid (LS), at least 10% of the lignin moieties are ethoxylated, at least about 30% of the sugar moieties of the hemicellulose from the lignocellulosic biomass are hydrolyzed to monosaccharide form and 20-70% of the sugar moieties of the hemicellulose from the lignocellulosic biomass are converted to ethyl glycosides (also referred to as ethoxylated sugars or sugar ethoxylates);

(c) releasing pressure from the pretreated material, and recovering sulfur dioxide and optionally ethanol from gas released from the pretreated material as a result of releasing pressure;

(d) washing the solid fraction comprising mainly cellulose obtained from the second container with a solution comprising water and ethanol (ranging from about 0% to about 100% in ethanol concentration, e.g., about 0.1% to about 99.9% ethanol, typically about 50% ethanol), and further washing the solid fraction with water, to provide washed cellulose and a wash filtrate, thereby removing ethanol and dissolved material from the cellulose, wherein the wash filtrate contains the dissolved material, which comprises lignin, ethoxylated lignin, lignosulfonic acid (LS), hemicellulose oligomers, ethyl glycosides (or ethoxylated sugars), and monosaccha rides;

(e) recovering ethanol from the wash filtrate by steam stripping, evaporation, successive flash stages, or by other methods, thereby precipitating lignin and ethoxylated lignin fractions, and optionally removing the precipitated lignin and ethoxylated lignin fractions;

(f) combining the washed cellulose with the wash filtrate from step (e) after ethanol has been recovered from the wash filtrate;

(g) adjusting pH of the combined stream from step (f) and contacting it with a cellulase, a glucosidase, a hemicellulase, or a combination thereof, to produce glucose and hemicellulose-derived monomeric sugars and release a small amount of insoluble lignin (where 'a small amount of insoluble lignin' refers to less than about 4%, less than about 5%, less than about 6%, or less than 10%, by weight, of washed cellulose fraction, in addition to any insoluble lignin in step (f)) and ethanol;

(h) optionally neutralizing the composition from step (g) to appropriate pH level and subjecting it to fermentation to produce ethanol.

In some embodiments, recovering sulfur dioxide in step (c) comprises:

(i) releasing gaseous vapors from the pretreated material at elevated temperature (typically at an initial temperature of 145° C. to 165° C., reducing over time with the release of gaseous vapors) and optionally at a lower pressure, wherein the gaseous vapors released from the pretreated material comprise sulfur dioxide and typically one or more of water vapor, ethanol vapor, and other volatiles ('other volatiles' refers to one or more of methanol, furfural, ethyl acetate, and acetic acid);

(ii) condensing at least a portion of the gaseous vapors to provide sulfur dioxide gas and a liquid containing at least one of water and ethanol; optionally purifying the sulfur dioxide gas by removing traces of other compounds including but not limited to one or more of water vapor, ethanol, and other volatiles;

(iii) liquefying sulfur dioxide gas by pressure change (e.g., an increase in pressure) and/or temperature reduction of the sulfur dioxide gas, providing liquid sulfur dioxide; and optionally storing the liquid sulfur dioxide; and (iv) introducing the liquid sulfur dioxide to the second container of step (b) or another pretreatment vessel, optionally by pumping.

In some embodiments, the step (b) pretreatment is performed in a continuous mode. In other embodiments, the step (b) pretreatment is performed in a batch mode. In a continuous mode, the biomass and the pretreatment chemicals, i.e. sulfur dioxide, ethanol and water, are continuously fed to the second container and the pretreatment products and unreacted chemicals are continuously removed from the second container, while the second container is maintained at constant pressure and temperature. In a batch mode, the biomass and the pretreatment chemicals are fed to the second container, followed by heating the container and retaining biomass with the pretreatment chemicals for a desired time in the second container, and subsequent discharge of the pretreatment products and unreacted chemicals.

In some embodiments, the step (g) enzymatic hydrolysis is performed in a continuous mode where the neutralized cellulose slurry and the enzymes are continuously fed into a liquefaction reactor, the liquefied slurry is continuously removed from the liquefaction reactor and continuously fed into a hydrolysis reactor, and the glucose fraction is continuously removed from the hydrolysis reactor; and when pulp is mixed with heat treated hemicellulose liquor in the process, before hydrolysis, the glucose and hemicellulose sugars mixture is continuously removed from the hydrolysis reactor. Alternatively, the neutralized cellulose slurry and the enzymes are continuously fed into a hydrolysis reactor, and the glucose fraction is continuously removed from the hydrolysis reactor; and when the pulp is mixed with heat treated hemicellulose liquor, before hydrolysis, the glucose and hemicellulose sugars mixture is continuously removed from the hydrolysis reactor. Alternatively, the heat-treated hemicellulose liquor is continuously fed into the hydrolysis reactor where it is mixed with the incoming liquefied cellulose stream (slurry), and the glucose and hemicellulose sugars mixture is continuously removed from the hydrolysis reactor. The liquefaction and hydrolysis reactors are maintained at constant desired pH, temperature, and mixing rate.

In other embodiments, the step (g) enzymatic hydrolysis is performed in a batch mode. For example, the neutralized cellulose slurry and the enzymes are fed into a hydrolysis reactor, followed by retaining the material at desired temperature, pH, and time, followed by discharging the glucose fraction or glucose and hemicellulose sugars mixture from the hydrolysis reactor.

In various embodiments, the process further comprising bleaching the solid fraction comprising mainly cellulose obtained in step (b), referred to as the washed pulp, to produce bleached cellulose that can be converted to dissolving pulp, including but not limited to viscose, cellulose ethers, and cellulose esters.

Surprisingly, the yield of non-condensed lignin produced by the process described herein is over 200 kg per BD metric tonne of softwood biomass, which is higher than that obtained in the AVAP® process (with sulfur dioxide) and higher than that obtained in common organosols processes (without sulfur dioxide). In some embodiments, the yield of non-condensed lignin is over 210 kg per BD metric tonne of softwood biomass. Accordingly, the yield of the non-condensed lignin is at least 65%, at least 70%, at least 72%, at least 74% or at least 76%, based on the amount of lignin in original biomass of the process. It is hypothesized that sulfur dioxide at moderate concentrations (e.g., 6-8 weight % sulfur dioxide) catalyzes formation of ethoxylated lignin without formation of excess of lignosulfonic acids, which results in very high non-condensed reactive lignin yields. Ethoxylated lignin can be separated and utilized as-is or after de-ethoxylation by heat treatment at temperatures below 120° C., alternatively, below 100° C., producing hydroxylated lignin, for example, according to the equation $C_9$—$O(C_2H_5)$+$H_2O$=$C_9$—$OH$+$C_2H_5OH$ where $C_9$ represents a phenylpropane unit in lignin.

The high yields of the processes refer to the yield of non-condensed lignin. High yields also refer to the yields of the monosaccharides. The yield of the monosaccharides obtained from the process is at least 70%, at least 74%, at least 78%, at least 82%, at least 86%, or at least 90% based on original saccharides in biomass. High yields of ethanol are also obtained from the process. The yield of ethanol is at least 35 g of ethanol per 100 g of monosaccharides, at least 40 g of ethanol per 100 g of monosaccharides, at least 43 g of ethanol per 100 g of monosaccharides, or at least 45 g of ethanol per 100 g of monosaccharides (amount present at initiation of fermentation).

Lignin produced in acidic processes, for example, processes based on sulfuric acid, produce condensed lignin in high concentrations, which results in sticky lignin products. The sticky lignin clogs any narrow openings in the processing apparatus, including pipes and valves, particularly in the digester, which reduces the process efficiency and increases maintenance costs. Surprising, despite the acidic nature of the pretreatment, and using only a moderate sulfur dioxide concentration, the lignin produced by the processes described herein is non-sticky, resulting in less or eliminated clogging of pipes, valves and other components of the processing equipment.

Also, contrary to known facts (sulfite pulping experience, the AVAP® process, and the Kaufmann diagram), using the process described herein, clean cellulose (i.e., cellulose with less than 5%, or less than 4%, residual lignin) is produced using moderate $SO_2$ concentrations, i.e. 8% or less, or 7% or less. This allows for the use of substantially decreased $SO_2$ charges compared to the state-of-the art AVAP® process. The $SO_2$ concentrations used in the process described herein are about half compared to those used in AVAP® process (6-8 weight % sulfur dioxide, compared to the 12%, 15%©, or greater than 15% for the AVAP® process).

Furthermore, the pretreatment process described herein surprisingly does not require explosion of the fiber structure to achieve high enzymatic digestibility, contrary to state-of-the-art processes. Thus, cellulose washing can be performed in the same manner as for conventional pulp and paper production with standard industrial equipment, including filter presses.

Furthermore, it was surprisingly discovered that sulfur dioxide at moderate concentrations, as used in the process disclosed herein (e.g., 6-8 wt %) in the presence of ethanol protects sugars from degradation. Sugar degradation in the process described herein is much lower than in conventional uncatalyzed organosolv process, resulting in higher sugar yields. A flow diagram of the disclosed process, according to one embodiment, is illustrated in FIG. 1.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention described herein.

DETAILED DESCRIPTION

Figure 1:
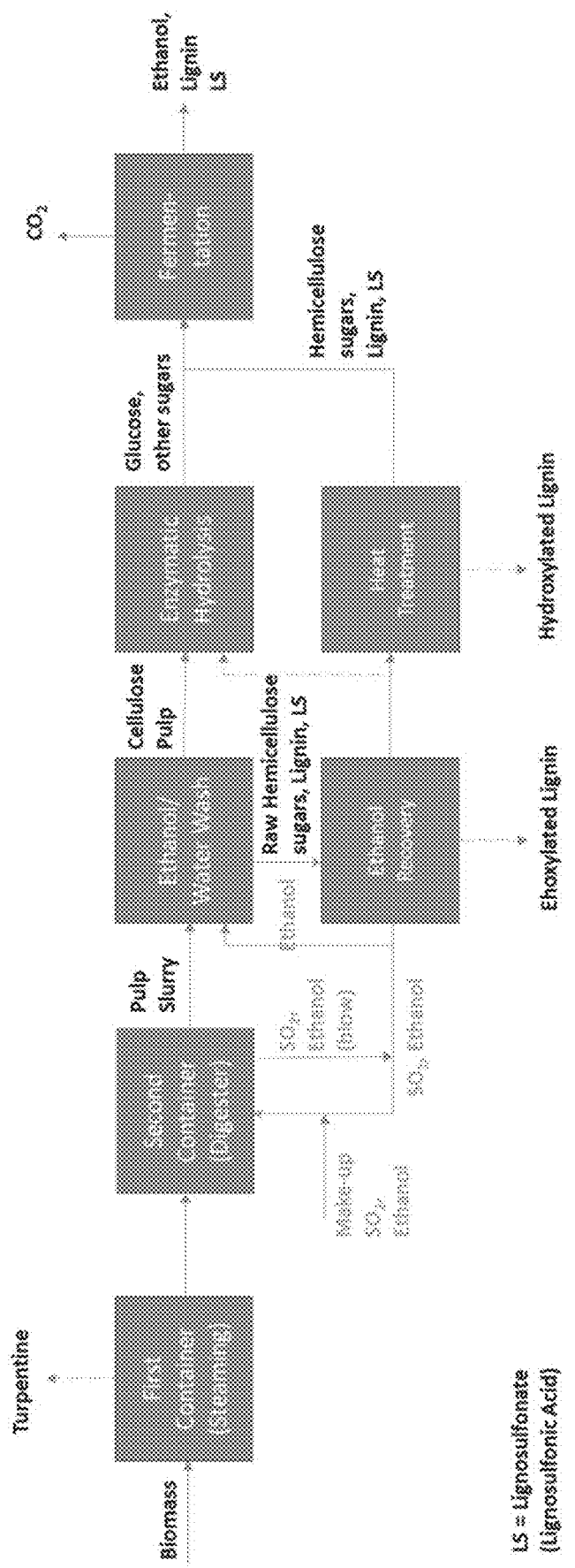
FIG. 1. A flowsheet example of the process for the production of ethoxylated and hydroxylated lignin fractions, lignocellulosic sugars, and ethanol in high yields. The lignin fractions, including ethoxylated and hydroxylated lignin, can be isolated at various points in the process to provide commercial products, in addition to the production of bioethanol, glucose, and hemicellulosic sugars or mixed sugars.

This disclosure provides a process for the production of ethoxylated and hydroxylated lignin fractions, cellulose, lignocellulosic sugars, and ethanol, in high yields. The process comprises steaming, pretreatment, chemicals recovery, saccharification, and optionally fermentation. The combination of pretreatment conditions results in simultaneously high yields of ethoxylated or hydroxylated lignin, cellulose or cellulosic sugars, and hemicellulosic sugars. High yield production of ethanol through fermentation of the sugars can also be obtained using the process.

Definitions

The following definitions are included to provide a clear and consistent understanding of the specification and claims.

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" is typically well understood by those of skill in the art and can refer to an exact ratio or configuration, or a ratio or configuration that is in the proximity of an exact value such that the properties of any variation are inconsequentially different than those ratios and configurations having the exact value. The term "substantially" may include variation as defined for the terms "about" and "approximately", as defined herein above.

The phrase "filter paper unit" or "FPU" refers to the measurement of cellulase activity using International Union of Pure and Applied Chemistry (IUPAC) guidelines (see Adney et al., Measurement of Cellulase Activities, Laboratory Analytical Procedure, Technical Report NREL/TP-510-42628, National Renewable Energy Laboratory, January 2008) and measures cellulase activity in terms of "filter-paper units" (FPU) per milliliter of original (undiluted) enzyme solution. The value of 2.0 mg of reducing sugar as glucose from 50 mg of filter paper (4% conversion) in 60 minutes has been designated as the intercept for calculating filter paper cellulase units (FPU) by IUPAC.

Figure 5:
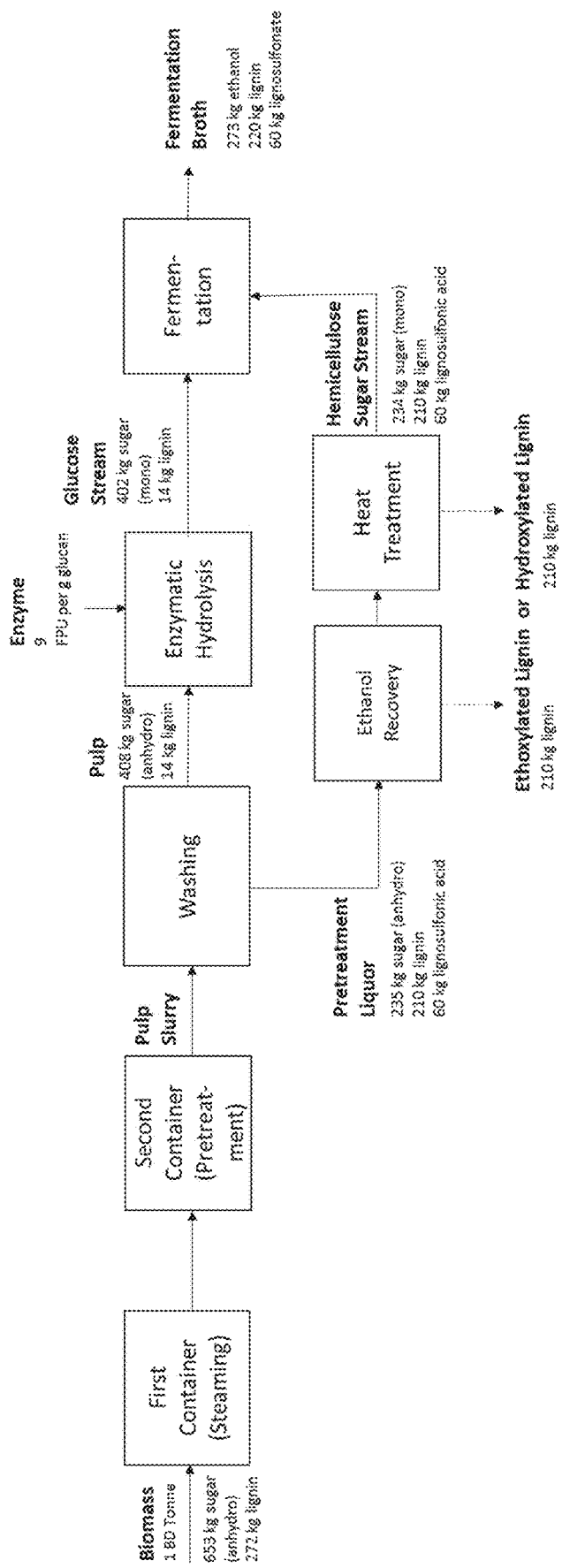
FIG. 5. Example of process flow diagram with product yields based on 1 tonne of dry biomass using 9 FPU per gram glucan. Ethoxylated lignin can be recovered (removed from the processing stream) at the ethanol recovery stage, it can be further processed to hydroxylated lignin and removed after heat treatment, or it can be maintained in the processing stream and removed after fermentation. Calculations show that over 87% of available saccharides in the original biomass are converted to monosaccharides.
Figure 6:
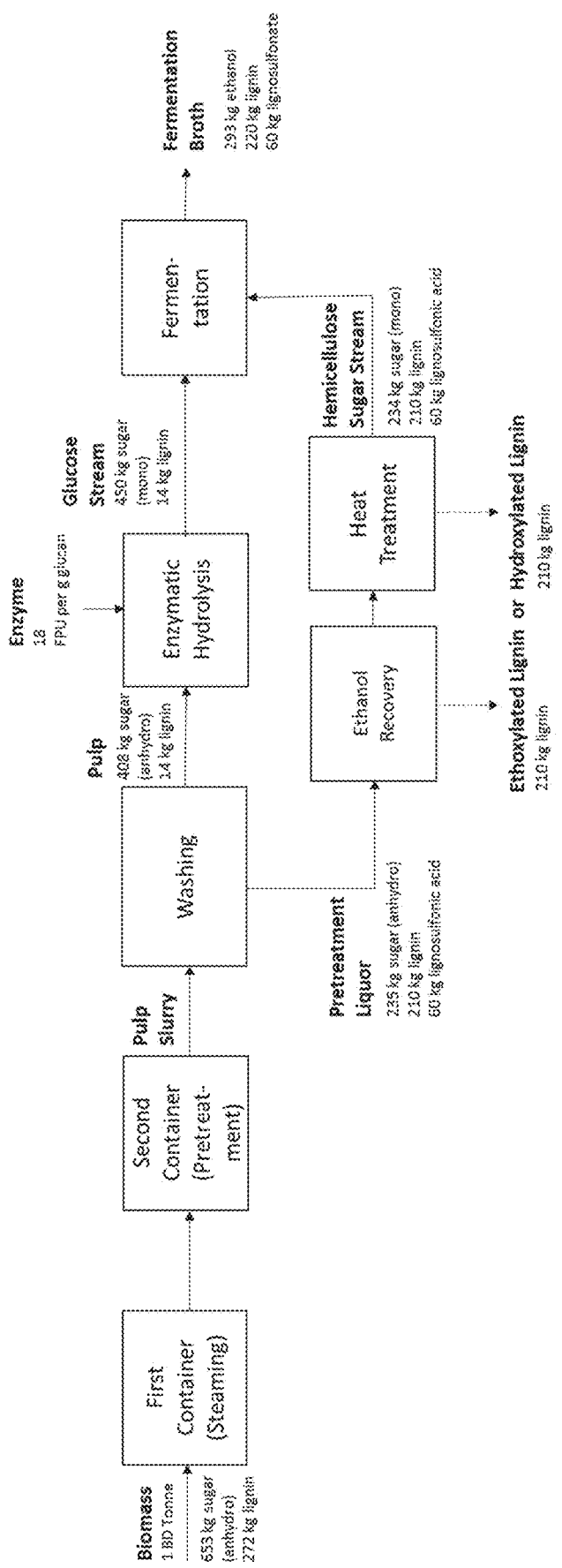
FIG. 6. Example of process flow diagram with product yields based on 1 tonne of dry biomass using 18 FPU per gram glucan. Ethoxylated lignin can be recovered (removed from the processing stream) at the ethanol recovery stage, it can be further processed to hydroxylated lignin and removed after heat treatment, or it can be maintained in the processing stream and removed after fermentation. Calculations show that over 94% of available saccharides in the original biomass are converted to monosaccharides.

The yield of monosaccharides obtained from the processes described herein (e.g., as illustrated by FIGS. 5 and 6) take into account that approximately 10% of the weight of a monosaccharide is hydration water that was not present when the moiety was in polymerized form (e.g., as cellulose in wood) (about 10% in the case of hexose sugars (glucose, galactose, and mannose) and about 12% in the case of pentose sugars (xylose and arabinose)). The added weight of the isolated monosaccharide averages roughly 10.5% for softwoods. For example, the yield of monosaccharides obtained by the process illustrated in FIG. 5 is calculated as follows: 402 kg (glucose stream)+234 kg (hemi stream)=636 kg (100-10.5)/100/653 kg (starting sugar equivalents from 1 metric tonne biomass) 87% yield.

Bleaching refers to the process of removing lignin from a composition or decolorizing lignin. Bleaching is typically carried out in one or more steps (e.g., 1-3) by applying various bleaching chemicals in each step, which either remove lignin or decolorize lignin. Suitable bleaching chemicals include, but are not limited to, oxygen in alkali (so-called 'oxygen delignification', or O-stage), chlorine dioxide (D-stage), hydrogen peroxide in alkali (P-stage), ozone (Z-stage), alkali extraction (E-stage), and enzymatic bleaching. Bleaching is a common and well-known practice used in bleached pulp production (for paper, tissue, etc.) and in dissolving pulp production.

Embodiments of the Invention

In various embodiments, the process for the production of ethoxylated and hydroxylated lignin fractions, cellulose, lignocellulosic sugars and ethanol in high yields includes the following steps and results.

In some embodiments, the process for lignocellulosic biomass valorization results in the production of non-condensed reactive lignin, yielding at least 65%, at least 70%, at least 72%, at least 74%, at least 75%, or at least 76% non-condensed reactive lignin, based on amount of lignin in the original biomass. Simultaneously, at least 70%, at least 74%, at least 78%, at least 82%, at least 86%, or at least 90% of available saccharides are converted to monosaccharides in the process.

Lignocellulosic biomass in a form of chips, forest residues, sawdust, waste wood, or similar forms is charged into a steaming bin.

Biomass is steamed to remove air, to optionally remove and recover turpentine, and to saturate biomass with water.

Biomass is impregnated and pretreated in a pressurized vessel with chemicals comprising sulfur dioxide, ethanol, and water, according to the methods described herein, to provide pretreated material.

In some embodiments, about 20-70% of the sugar moieties of the hemicellulose from the lignocellulosic biomass are converted to ethyl glycosides during pretreatment. In other embodiments, about 30-60% of the sugar moieties of the hemicellulose from the lignocellulosic biomass are converted to ethyl glycosides during pretreatment.

After the pretreatment described above, excess sulfur dioxide and optionally some or substantially all of the ethanol is released from the pretreated material at elevated temperature, optionally at lower pressure than that of the pressurized vessel. Water vapor, ethanol vapor, and other condensable gases are condensed. The sulfur dioxide gas is optionally purified by removing traces of other compounds including but not limited to water vapor, ethanol vapor, and other volatiles. The sulfur dioxide is then liquefied by pressure change and/or temperature reduction of the gas, providing liquid sulfur dioxide. Liquid sulfur dioxide is then reintroduced into the pretreatment vessel, optionally by pumping. In continuous mode, the pressure is generally not released from the second container (digester); the pretreated material is blown or discharged to a blow tank, where pressure is released. The pressure in the digester in a continuous mode system is generally constant.

Decompression can be either sudden, i.e., explosive to disrupt the fiber structure, or non-explosive, i.e., using a mild blow similar to the conventional blow practiced in traditional pulping. The cellulose digestibility by enzymes is surprisingly high in the latter case.

The cellulose pulp is washed with one or more ethanol-water mixtures and water in order to remove dissolved material. The dissolved material comprises dissolved ethoxylated lignin, lignosulfonic acid, hemicellulose saccharides, sugars, sugar ethoxylates and ethanol. The washing can be done, for example, by centrifugation, but can also be performed using a conventional filter press or other conventional pulp mill equipment when fiber explosion is not practiced.

Cellulose is hydrolyzed to glucose using cellulolytic enzymes. The cellulolytic enzymes can comprise one or more of cellulases, glucosidases, and hemicellulases. Hydrolysis of the cellulose also results in the release a small amount of insoluble lignin and hemicellulose sugars from the cellulose. In this context, a 'small amount of insoluble lignin' comprises less than about 4%, less than about 5%, less than about 6%, or less than 10%, by weight, of washed cellulose fraction.

Ethanol is removed from the wash liquor, for example, by steam stripping, evaporation, or successive flash stages. The recovered ethanol can be recycled and reused in the process. Upon removal of ethanol, ethoxylated lignin precipitates in a large quantity compared to prior art and can be recovered if desired, for example, by using a stacked disc centrifuge.

Ethoxylated lignin, hydroxylated lignin, or both may be obtained from the process. Ethoxylated lignin is produced in the pretreatment stage, all or a portion of which can be removed prior to heat treatment. Alternatively, the ethoxylated lignin can be maintained in the processing stream and carried through to the heat treatment stage, at which time it is converted to hydroxylated lignin, which can also optionally be separated from the stream.

The liquor can then be heated at 90-120° C. for 0.5-8 hours to hydrolyze ethoxylated sugars, sugar oligomers and, if present, ethoxylated lignin, to maximize monomeric sugar yield, produce hydroxylated lignin and to recover ethanol bound to sugars and lignin. Hydroxylated lignin may be separated at this point, if desired, for example, by decanting centrifuge.

Prior to heat treatment, the hemicellulose liquor is optionally combined with unhydrolyzed cellulose and the resulting mixture is subjected to enzymatic hydrolysis to produce glucose and hemicellulosic sugars using cellulolytic enzymes, for example, one or more of cellulases, glucosidases, and hemicellulases.

After heat treatment, the hemicellulose liquor is optionally combined with unhydrolyzed cellulose and the resulting mixture is subjected to enzymatic hydrolysis to produce glucose and hemicellulosic sugars using cellulolytic enzymes, for example, one or more of cellulases, glucosidases, and hemicellulases. As would be readily recognized by one skilled in the art, the temperatures of the hydrolysis can be enzyme-specific but are commonly carried out at about 50° C. to about 58° C., or at about 50° C. to about 56° C. Likewise, the operating pH is typically about 4.5 to about 6, or about 4.8 to about 5.8.

Cellulosic and hemicellulosic sugar streams can be combined and, after appropriate neutralization, fermented to ethanol and carbon dioxide. The fermentation can be carried out according to product guidelines of a particular *Saccharomyces cerevisiae*, or genetically modified version thereof, typically at a pH of about 4.5 to 6, or about 5.0 to 5.8, and at a temperature of about 30° C. to about 34° C. Separate usage of cellulosic and hemicellulosic streams can also be carried out. Cellulose-based glucose can be used as a source for chemical or biochemical transformations to provide value-added products. Cellulose can be used for preparation of dissolving pulp, for example, viscose, cellulose ethers, and cellulose esters.

Alternatively, the ethoxylated or hydroxylated lignin can be separated after fermentation.

The pretreatment conditions of various embodiments are shown in Table 1 below.

TABLE 1

The pretreatment conditions.

| Parameter | Unit | Range |
| --- | --- | --- |
| Sulfur Dioxide Charge | weight % in liquor | 6-8 |
| Ethanol Charge | weight % in liquor | 30-60 |
| Liquor-to-Solid Ratio (L/S) | kg liquid/kg BD biomass | 2.5-4.5 |
| Temperature | ° C. | 145-165 |
| Duration | min | 20-120 |

The pretreatment conditions described herein result in production of high yields of non-condensed, reactive and non-sticky ethoxylated or hydroxylated lignin with simultaneous high yields of fermentable sugars, or optionally cellulose and fermentable hemicellulosic sugars. Lignin is obtained in ethoxylated or hydroxylated form at higher than 72% or higher than 76% based on original lignin amount in biomass or, for softwoods, at higher than 200 BD kg per BD metric tonne biomass, or higher than 210 BD kg per BD metric tonne biomass, while wood polysaccharides conversion to monomeric sugars is higher than 82%, higher than 86%, or higher than 90%, or for softwoods, higher than 600 BD kg per BD tonne biomass, or higher than 620 BD kg per BD tonne biomass.

Optionally, cellulose is obtained at about 400 BD kg per BD tonne biomass and hemicellulosic fermentable sugars are obtained at higher than 200, or higher than 220 BD kg per BD tonne softwood biomass. The absolute yields depend on original composition of lignocellulosic biomass. The lignosulfonate amount will correspond to the mass of lignin that has not been precipitated in the form of ethoxylated or hydroxylated lignin.

The processes described herein involve a Pretreatment Phase, an Enzymatic Hydrolysis Phase, and optionally, a Fermentation Phase, which processes can be further described as follows. The Pretreatment Phase is outlined by Steps (a) and (b), which can utilize the pretreatment conditions of Table 1 above or variations thereof, the Enzymatic Hydrolysis Phase is outlined by Steps (c) through (g), and the Fermentation Phase is outlined by Steps (h) and (i), as follows.

Step (a). Lignocellulosic biomass is steam treated in a steaming bin. The lignocellulosic biomass absorbs water from the steam. The lignocellulosic biomass is preferably saturated with water. Air is removed from the lignocellulosic biomass before transferring the wet lignocellulosic biomass to a second container. When the biomass contains volatile extractives, these can be removed along with the air. For biomass containing relatively high amounts of volatile extractives (e.g., pine), turpentine is removed at about 0.3-0.5 wt % based on dry biomass.

Step (b). The lignocellulosic biomass is transferred from the steaming bin to digester (a pressurized and heated container) and is then combined with a cooking liquor to impregnate the lignocellulosic biomass. The resulting impregnated lignocellulosic biomass is optionally transferring to a separate container for completing the digestion.

The cooking liquor is made up of water ethanol, and sulfur dioxide. In one embodiment, the cooking liquor comprises 6-8 weight % sulfur dioxide, 30-60 weight % ethanol, and 32-64 weight % water (including water from the steamed lignocellulosic biomass). In another embodiment, the cooking liquor comprises 3-8 wt. % sulfur dioxide (typically 5-8 weight % or 6-8 weight %), 20-60 wt. % ethanol, and 32-73 wt. % water.

In various embodiments, the ratio of cooking liquor to lignocellulosic biomass, based on dry weight of the lignocellulosic biomass, can be about 2:1 to about 4.5:1, about 2.5:1 to about 3.5:1, about 2:1 to about 3.5:1, about 2.5:1 to about 4:1, about 2.5:1 to about 3:1, about 3:1 to about 3.5:1, about 3:1 to about 4:1, about 2.8:1 to about 3.2:1.

During digestion, the impregnated lignocellulosic biomass is heated under pressure for 30-120 minutes at about 145° C. to about 165° C. Pressure increases with increasing temperature, and with increasing $SO_2$ and ethanol content. The pressure in the digester created by the process conditions described herein is typically in the range 10-17 bar (140-250 psi).

Heating in the cooking liquor releases and/or dissolves lignin and hemicellulose from the lignocellulosic biomass into the cooking liquor, leaving behind a solid fraction, mostly cellulose ("pulp" or "fiber").

During digestion a hydrolysate is formed. About 10-40% of the lignin from the lignocellulosic biomass is sulfonated to produce lignosulfonic acid (LS) in the hydrolysate. The hydrolyzate therefore contains 60-90% lignin, and 10-40% lignosulfonic acid (LS) based on the total initial lignin weight. In other embodiments, about 20-50%, of the lignin from the lignocellulosic biomass is sulfonated to produce lignosulfonic acid (LS) in the hydrolysate. The hydrolysate then contains 50-80% lignin and 20-50% lignosulfonic acid (LS) based on the total initial lignin weight. At least about 25%, at least about 30%, or at least about 35%, of the hemicellulose from the lignocellulosic biomass is hydrolyzed to monosaccharide form at this stage. The remaining hemicellulose sugars in the hydrolysate are hemicellulose oligomers or ethoxylated sugars.

Step (c). The pressure is then released from the tank containing the hydrolysate. Sulfur dioxide is recovered as the pressure is released. Ethanol can be recovered by the same process. The sulfur dioxide and optionally the ethanol can then be recycled back to the digester.

Step (d). The solid cellulose fraction obtained from the digestion is washed with water, or optionally with a solution containing water and ethanol ranging from 0% to about 99% ethanol by weight. The cellulose is then further washed with water to remove any remaining ethanol and lignin, followed by its separation from the liquids, to provide washed cellulose and a wash filtrate. The wash filtrate contains the dissolved material including lignosulfonic acid (LS), lignin, hemicellulose oligomers, ethoxylated sugars, and monosaccharides.

Step (e). Ethanol is then recovered from the wash filtrate, optionally by steam stripping, to provide a concentrated wash filtrate. The recovered ethanol can then be recycled for use in a digester or optionally for washing procedures.

Step (f). The concentrated wash filtrate is then heated in the range of about 90° C. to about 120° C. for 0.5-8 hours to hydrolyze the hemicellulose oligomers and ethoxylated sugars to monosaccharides, which maximizes monomeric sugar yields and liberates ethanol bound to monosaccharides and lignin. The resulting mixture is referred to as the first fermentable composition (FC1). Each of the fermentable compositions described herein (e.g., FC1-FC5) contain water and one or more sugars. The FC1 contains monosaccharides, lignosulfonic acid, and lignin. Lignin, often present in the form of a colloidal or fine precipitate before the heat treatment or as denser solids after the heat treatment, may optionally be removed.

Step (g). The washed cellulose of step (d) is then combined with a cellulase, a glucosidase, or a combination of glycosidases under standard enzyme hydrolysis conditions to produce glucose. Small amounts of lignin (if present) are also released at this stage. The resulting composition is referred to as the second fermentable composition (FC2). A cellulase, a glucosidase, or a combination of glycosidases is added in a reactor containing the FC2 to provide a liquefied fraction. The mixture is then transferred to second reactor to finalize hydrolysis of the cellulose without the need for any additional glycosidases.

Step (h). The pH of the FC1, the FC2, or the FC1 and FC2 combined, can optionally be adjusted for optimal fermentation conditions. The pH of the FC1 can be about 0.6-2.0, typically 0.8-1.5, depending on its concentration and other conditions. Partial neutralization to a pH in the range of 4.0-6.0 can be performed to provide increased ethanol production under standard fermentation conditions. The resulting pH adjusted compositions are referred to as the FC3, FC4, or FC5, respectively.

Step (i). One or more of the fermentable compositions FC1-FC5 are then combined with yeast under suitable fermentation conditions to produce lignocellulosic ethanol and carbon dioxide. The ethanol can then be recovered by distillation, for example, in a beer column. Solids (lignin and lignosulfonates) can also be recovered and utilized as a fuel source.

In one particular embodiment, the process for the production of ethoxylated and hydroxylated lignin fractions, cellulose, lignocellulosic sugars, and ethanol, in high yields, comprises:

(a) contacting lignocellulosic biomass with steam in a first container to provide steamed lignocellulosic biomass;

(b) contacting the steamed lignocellulosic biomass in a second container with a pretreatment liquor at a temperature between 144° C. and 166° C. under pressure for 40-120 minutes;

wherein the pretreatment liquor comprises 7-8 weight % sulfur dioxide, 40-60 weight % ethanol, and 32-54 weight % water (including water from the steamed lignocellulosic biomass), and the ratio of pretreatment liquor to lignocellulosic biomass, based on dry weight of the lignocellulosic biomass, is about 2.5 to about 4 kg/kg (including water from the steamed lignocellulosic biomass in the mass of the pretreatment liquor);

thereby releasing and/or dissolving lignin and hemicellulose from the lignocellulosic biomass into the pretreatment liquor, resulting in a mixture comprising lignin and hemicellulose dissolved in the pretreatment liquor and a solid fraction comprising cellulose from the lignocellulosic biomass, which mixture is referred to as the pretreated material;

wherein about 10-40% of the lignin from the lignocellulosic biomass is sulfonated to produce lignosulfonic acid (LS), at least 10% of the lignin moieties are ethoxylated, at least about 30% of the sugar moieties of the hemicellulose from the lignocellulosic biomass are hydrolyzed to monosaccharide form, 30-80% of the sugar moieties of the hemicellulose from the lignocellulosic biomass are converted to ethoxylated sugars, the cellulosic pulp yield is at least 40%, the acetyl groups in the solid fraction comprising cellulose is less than 0.1%, and the solid fraction comprising cellulose comprises less than 2.1% lignin;

(c) releasing pressure from the pretreated material and recovering sulfur dioxide and ethanol from gas released from the pretreated material as a result of releasing pressure;

(d) washing the solid fraction comprising cellulose obtained from the second container with a solution comprising water and ethanol (ranging from 40% to 60% in ethanol concentration), and further washing the solid fraction with water, to provide washed cellulose and a wash filtrate, thereby removing ethanol and dissolved material from the cellulose, wherein the wash filtrate contains the dissolved material, which comprises lignin, ethoxylated lignin, lignosulfonic acid (LS), hemicellulose oligomers, ethoxylated sugars, and monosaccharides;

(e) recovering ethanol from the wash filtrate, thereby precipitating lignin and ethoxylated lignin fractions;

(f) heating the material obtained after step (e) at a temperature between 100° C. and 125° C. for 0.5-2 hours to hydrolyze the ethoxylated sugars and hemicellulose oligomers to monosaccharides and to hydrolyze ethoxylated lignin to release ethanol and to provide a composition, referred to as a hemicellulose stream, comprising of lignosulfonic acid and monosaccharides, and hydroxylated lignin and lignin;

(g) adjusting the pH of the washed cellulose stream from step (d) to a pH between 4.8 and 5.8 and contacting it with a combination of cellulases, glucosidases, and hemicellulases at a temperature of about 50° C. to about 56° C. to produce glucose, which is referred to as a glucose fraction;

(h) combining the glucose fraction of step (g) with the hemicellulose stream of step (f) to provide a fermentable composition, wherein the combined glucose fraction and hemicellulose stream comprises less than 0.9% of furfural, hydroxymethylfurfural, and levulinic acid combined, and the combined glucose fraction and hemicellulose stream comprises a total saccharide recovery from the lignocellulosic biomass of at least 96%; and (i) adjusting the pH of the fermentable composition of step (h) to a pH between 5.0 and 6.0, or to a pH between 5.4 and 6.0, and subjecting the pH-adjusted fermentable composition to fermentation by yeast at a temperature between 30° C. and 34° C. to produce ethanol. The process can yield at least 72%, at least 74%, or at least 76% non-condensed reactive lignin, based on amount of lignin in the lignocellulosic biomass used in the process. The non-condensed reactive lignin can obtained in the form of ethoxylated lignin, hydroxylated lignin, or a combination thereof.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Biomass Pretreatment

Scots pine sawdust (560 g of biomass) containing 54.4% moisture (as-received basis) and dry mass components including 43.9% glucan (oven dry basis), 5.2% xylan, 3.4% galactan, 2.0% arabinan, 10.9% mannan, 1.4% acetyl groups, 27.2% lignin, 1% acetone extractives, and 0.1% ash, was pretreated in eight rotating mini-reactors submerged in heated oil. A liquor for pretreatment was prepared resulting in a moisture-adjusted composition of 7% sulfur dioxide, 46.5% or 58% ethanol and 46.5% or 35% water, by weight, and the liquor was charged at about 4 parts liquor per 1 part of dry biomass (i.e., at liquor-to-solid ratio of 4 kg/kg). The biomass and liquor were combined and the pretreatment was carried out at a final temperature of 155° C., which final temperature was achieved about 15 minutes after initiation of the pretreatment. The amount of time at the final temperature was 60 minutes; cooling down time was about 2 minutes (cooling by submerging the reactors in ice water). No fiber explosion was used. The resulting cellulosic pulp was separated from the spent liquor using a nylon bag and was washed twice with 50% ethanol in water and twice with water.

The cellulosic pulps were notably bright, indicating excellent delignification and the absence of lignin condensation and deposition (see Table 2). The color of the cellulosic pulps was surprisingly bright considering the relatively low sulfur dioxide charge (7%). Compositional analysis of pulps showed that they are primarily cellulose with very little impurities of lignin (≤2% based on the original biomass) and hemicelluloses (≤3.3% based on the original biomass). Sugar degradation was also surprisingly low. Measured sugar degradation products account for less than 0.8-1.2% based on the original biomass, which is unexpectedly low based on the relatively high temperature and low sulfur dioxide charge, in view of the well-known correlation between degradation of sugars and temperature in acidic pretreatments.

TABLE 2

Pretreatment streams yields and composition.

| Pretreatment conditions set No. | 1 | 2 | 3 |
|---|---|---|---|
| Ethanol concentration, weight % | 46.5 | 58 | 58 |
| Pretreatment temperature, ° C. | 155 | 155 | 160 |
| Cellulosic Pulp | | | |
| Pulp color | Light | Very light | Light |
| Cellulosic pulp yield, % on o.d. biomass | 40.6 | 43.5 | 37.6 |
| Glucan in pulp, % on o.d. biomass | 38.2 | 37.9 | 35.0 |
| Hemicelluloses in pulp, % on o.d. biomass | 2.0 | 3.3 | 1.6 |

TABLE 2-continued

Pretreatment streams yields and composition.

| Pretreatment conditions set No. | 1 | 2 | 3 |
|---|---|---|---|
| Acetyl groups in pulp, % on o.d. biomass | 0.0 | 0.0 | 0.0 |
| Lignin in pulp, % on o.d. biomass | 1.4 | 2.0 | 2.0 |
| Kappa number of pulps | 17 | 25 | 32 |
| Dissolved Saccharides | | | |
| Monomeric sugars (as anhydro), % on o.d. biomass | 14.8 | 12.8 | 15.6 |
| Oligomeric and ethoxylated sugars (as anhydro), % on o.d. biomass | 8.7 | 9.6 | 7.5 |
| Total Saccharides Recovery | | | |
| Total saccharides recovery from biomass (after pretreatment), % | 98 | 97 | 91 |
| Sugar Degradation Products | | | |
| Furfural, % on o.d. biomass | 0.5 | 0.2 | 0.6 |
| Hydroxymethylfurfural, % on o.d. biomass | 0.1 | 0.1 | 0.2 |
| Levulinic acid, % on o.d. biomass | 0.2 | 0.2 | 0.4 | o.d.—oven dried.

Example 2

Process for the Production of Bioproducts in High Yield

The Glucose Sugar Stream.

The washed cellulosic pulp obtained in Example 1 (pretreatment conditions set No. 1) was subjected to enzymatic hydrolysis in shake flasks, in duplicate. A commercially available enzyme cocktail containing cellulases, hemicellulases and β-glucosidases was used at charges of 5.4, 9.0 and 18 FPU per g glucan in pulp. The total solids content during enzymatic hydrolysis was 9%, the pH was maintained at 4.8-5.3 using an ammonium hydroxide solution, and the temperature was set to 54° C. The shaking rate was 250 RPM during liquefaction (first hour) and 150 RPM during the rest of hydrolysis (72 hours total).

Figure 2:
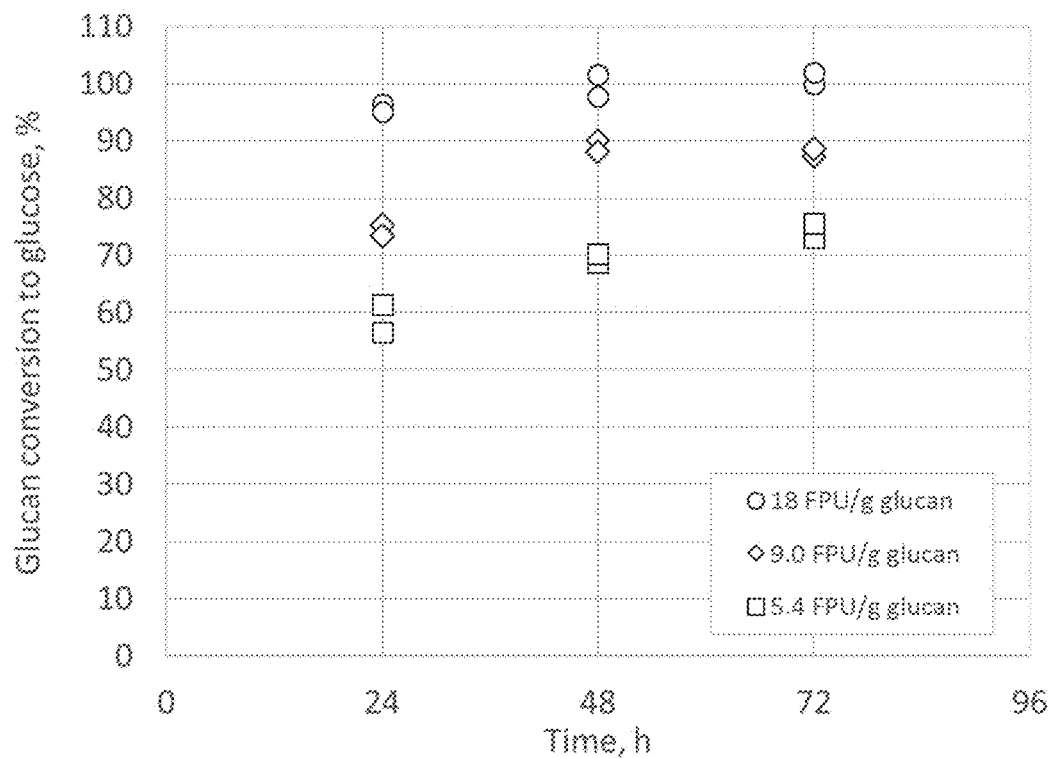
FIG. 2. Enzymatic digestibility of cellulosic pulp obtained using the described process (FPU: filter paper unit; FPU/g: the measure of enzyme charge per g glucan in cellulosic pulp).

The cellulosic pulp is highly digestible by enzymes with about 90% glucan-to-glucose conversion obtained already at an enzyme charge of 9.0 FPU/g glucan, despite the fact that no fiber explosion was used (see FIG. 2). The enzymatic hydrolysate obtained is referred to as the glucose sugar stream, or glucose fraction.

Ethoxylated Lignin.

Figure 3:
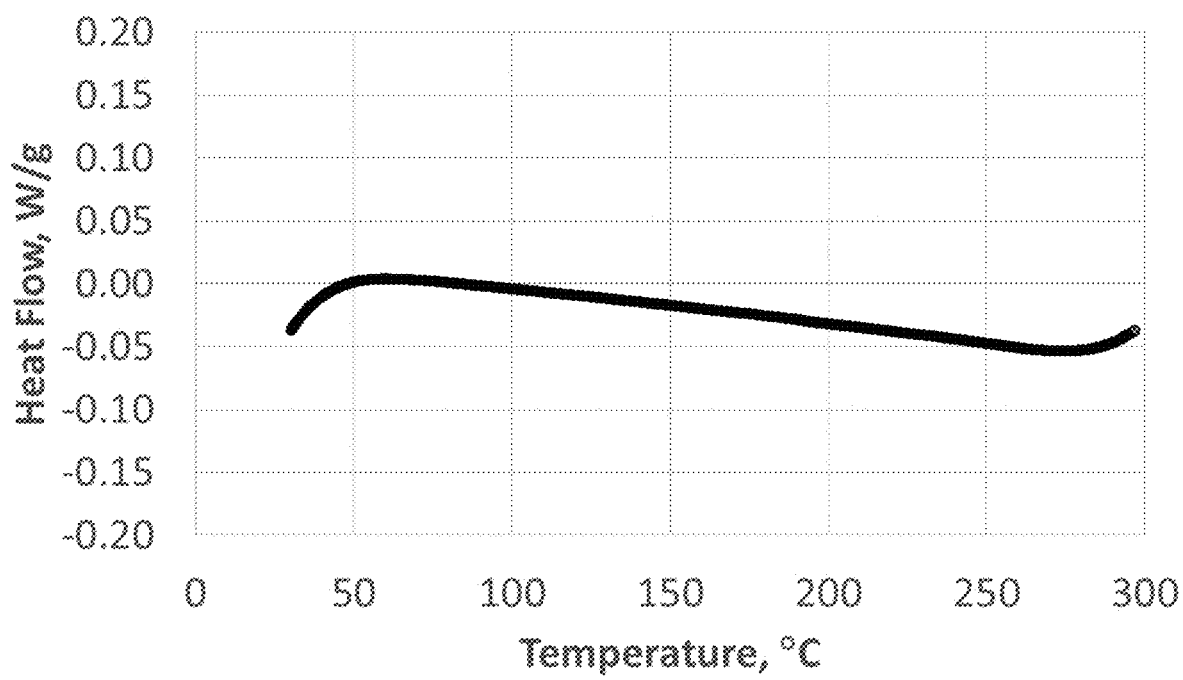
FIG. 3. Characterization of the Ethoxylated Lignin obtained in the described process (Differential Scanning Calorimetry curves (heat/cool/heat method)).
Figure 4:
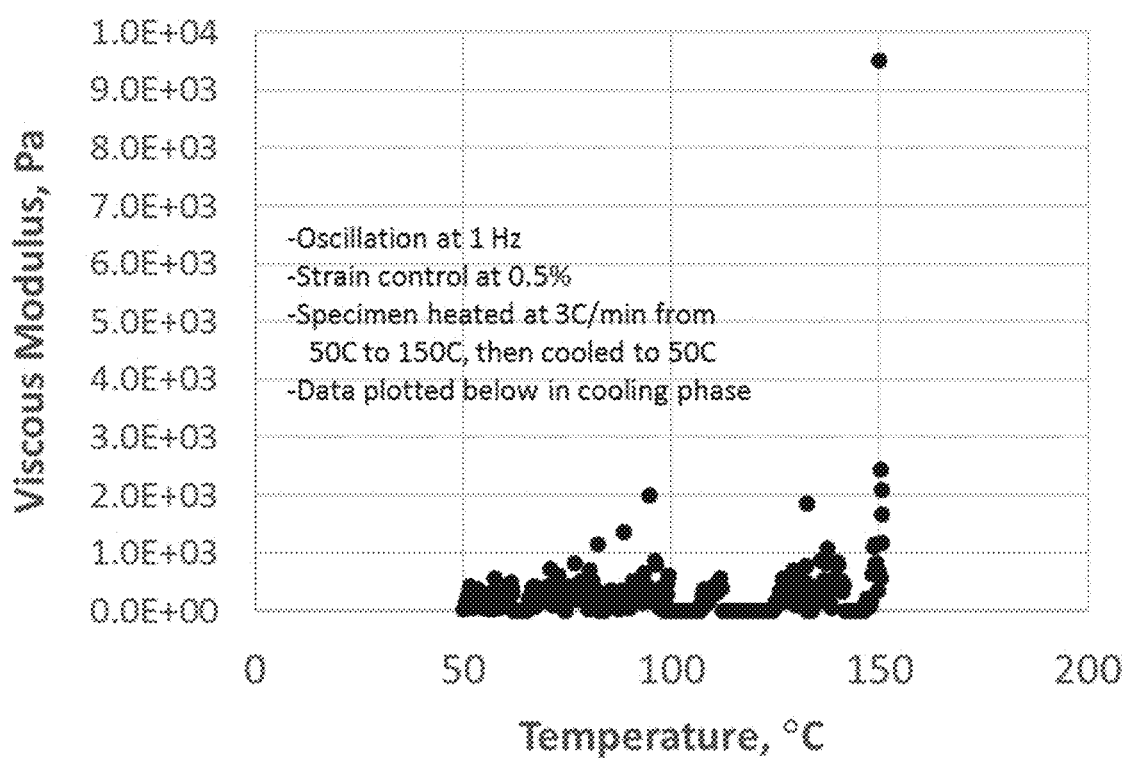
FIG. 4. Characterization of the Ethoxylated Lignin obtained in the described process: Viscous Modulus vs. Temperature.

A portion of the wash liquor obtained from Example 1 (pretreatment conditions set No. 1) was evaporated in a rotary evaporator to remove sulfur dioxide and ethanol. Precipitated ethoxylated lignin was separated by centrifugation and washed with water. The precipitated lignin, primarily (>50%) ethoxylated lignin, was obtained in a yield of 210 BD kg per BD metric tonne biomass, which corresponds to over 76% of original lignin in biomass feedstock, a surprisingly high amount. Air dried precipitated lignin was characterized by Differential Scanning Calorimetry (FIG. 3) and Viscous modulus vs. temperature (FIG. 4) measurements. Differential Scanning Calorimetry showed no evidence of lignin melting up to 300° C. Changes in viscous modulus with temperature were also not observed. When the sample was taken out after the viscosity test it was still in the same dry powder form, showing that the lignin did not melt. Thus, ethoxylated lignin is not sticky and does not become sticky when heated up to 150° C.

The Hemicellulose Sugar Stream.

A separate portion of wash liquor obtained from Example 1 (pretreatment conditions set No. 1) after rotary evaporation and without precipitated lignin removal was subjected to heat treatment at 120° C. for 60 minutes resulting in over 90% conversion of hemicellulose oligomers and ethoxylated sugars to monomeric sugars. The stream after heat treatment is referred to as the hemicellulose sugar stream.

Hydroxylated Lignin.

Simultaneously with conversion of hemicellulose oligomers and ethoxylated sugars to monomeric sugars, ethoxylated lignin was de-ethoxylated to form hydroxylated lignin, which can be separated at this point if desired or, optionally, after a beer column (e.g., after distillation of ethanol from the fermentation broth).

Combined Glucose Stream and Hemicellulose Sugar Stream.

The glucose sugar stream was mixed with the hemicellulose sugar stream in proportions corresponding to their sugar amounts in the original biomass. The mixture was neutralized to pH 5.8-6 and fermented in shake flasks (150 RPM) at pH=5.0-5.8, in duplicate, by a commercially available genetically modified yeast strain capable of utilizing all five wood sugars. Suitable examples of yeast cells and fermentation techniques are described in US Patent Publication No. 2019/0106464 (Oeser et al.). The process can optionally employ a combination of yeast strains capable of utilizing all five wood sugars. The initial sugar concentration was 75 g/L and the inoculation was carried out with 0.5 g dry yeast/L. The fermentation was carried out at 32° C. The fermentation took less 24 hours, at which time 98% of the sugars were consumed and the ethanol yield was 84.2% of theoretical or higher, i.e. 0.43 g ethanol/g sugar or higher. The process flow diagram and the product yields are depicted in FIG. 5, which illustrates an example of one embodiment of the invention.

Citations:
1. Aziz, S., Sarkanen, K, (1989) Organosolv pulping—a review. Tappi Journal 72(3), 169-175.
2. Chum, H. L., Johnson, D. K., Black, S. K. et al. (1990) Pretreatment-Catalyst effects and the combined severity parameter. Appl Biochem Biotechnol 24, 1.
3. Del Rio, L. F., Chandra, R. P. & Saddler, J. N. (2010) The Effect of Varying Organosolv Pretreatment Chemicals on the Physicochemical Properties and Cellulolytic Hydrolysis of Mountain Pine Beetle-Killed Lodgepole Pine. Appl Biochem Biotechnol 161, 1-21.
4. Del Rio, L. F., Chandra, R. P., Saddler, J. N. (2011) The effects of increasing swelling and anionic charges on the enzymatic hydrolysis of organosolv-pretreated softwoods at low enzyme loadings. Biotechnol. Bioeng. 108, 1549-1558.
5. Fernando, F. E., Vallejos, M. E., Area, C. M. (2010) Lignin recovery from spent liquors from ethanol-water fractionation of sugar cane bagasse. Cellul. Chem. Technol. 44, 311-318.
6. Kaufmann, Z. (1951) Uber die chemischen Vorgange beim Aufschluss von Holz nach dem Sulfitprozess. Diss., Eid. Tech. Hochsch. Zurich, Zurich.
7. Kleinert, T. N. (1974) Organosolv pulping with aqueous alcohol. Tappi 57(8), 99-102.
8. Nakagame, S., Chandra, R. P., Saddler, J. N. (2010) The effect of isolated lignins, obtained from a range of pretreated lignocellulosic substrates, on enzymatic hydrolysis. Biotechnol. Bioeng. 2010, 105, 871-879.
9. Nitsos, C., Stoklosa, R., Karnaouri, A., Vörös, D., Lange, H., Hodge, D., Crestini, C., Rova, U., Christakopoulos, P. (2016) Isolation and Characterization of Organosolv and Alkaline Lignins from Hardwood and Softwood Biomass. *ACS Sustainable Chemistry & Engineering* 4(10), 5181-5193.
10. Pan, X., Xie, D., Yu, R. W., Lam, D., Saddler, J. N. (2007) Pretreatment of Lodgepole Pine Killed by Mountain Pine Beetle Using the Ethanol Organosolv Process: Fractionation and Process Optimization. *Ind. Eng. Chem. Res.* 200, 46, 2609-2617.
11. Pan, X., Arato, C., Gilkes, N., Gregg, D., Mabee, W., Pye, K., Xiao, Z., Zhang, X., Saddler, J. (2005) Biorefining of softwoods using ethanol organosolv pulping: Preliminary evaluation of process streams for manufacture of fuel-grade ethanol and co-products. Biotechnol. Bioeng., 90, 473-481.
12. Pylkkanen, V. (1992) Characterization of the ethanol-$SO_2$ pulping and a preliminary chemical recovery process design. Master thesis, Lappeenranta University of Technology, Finland.
13. Sannigrahi, P., and Ragauskas, A. J. (2013) Fundamentals of Biomass Pretreatment by Fractionation. In Aqueous Pretreatment of Plant Biomass for Biological and Chemical Conversion to Fuels and Chemicals, First Edition. Edited by Charles E. Wyman. JohnWiley & Sons, Ltd.
14. Sjöström, E. (1981) Wood chemistry. Fundamentals and Applications, $2^{nd}$ Edition. Academic Press, Inc., San Diego.
15. Sklavounos, E., Iakovlev, M., Survase, S., Granström, T., van Heiningen, A. (2013a). Oil palm empty fruit bunch to biofuels and chemicals via SO2-ethanol-water fractionation and ABE fermentation. Bioresour. Technol. 147, 102-109.
16. Sklavounos, E., Iakovlev, M., van Heiningen, A. (2013b). Study on conditioning of SO2-Ethanol-Water spent liquor from spruce chips/softwood biomass for ABE fermentation. Ind. Eng. Chem. Res. 52, 4351-4359.
17. Sklavounos, E., Iakovlev, M., Yamamoto, M., Terasvuori, A.-L., Jurgens, G., Granström, T. B., van Heiningen, A. (2011). Conditioning of SO2-ethanol-water spent liquor from spruce for the production of chemicals by ABE fermentation. Holzforschung 65, 551-558.
18. Sklavounos, E., Iakovlev, M., Survase, S., Gouveia, S., Moldes, D., Sanroman, M. A., van Heiningen, A. (2014) Comparison of two conditioning schemes for detoxifying SO2-Ethanol-Water hydrolysate from lignocellulosics for ABE fermentation. Nordic Pulp & Paper Research Journal 29, 370-382.
19. van Heiningen, A., Sharazi, A. M., Tunc, M. S. (2018). Reactions of ethanol with xylan and lignin in organosolv pulping: implications for ethanol recovery and process selection. 15th European Workshop on Lignocellulosics and Pulp (EWLP), 26-29th June, Aveiro, Portugal.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A process for the production of ethoxylated and hydroxylated lignin fractions, cellulose, lignocellulosic sugars, and ethanol, in high yields, comprising:
    (a) contacting lignocellulosic biomass with steam in a first container, wherein the lignocellulosic biomass absorbs water from the steam, removing air and optionally turpentine from the lignocellulosic biomass;
    (b) contacting the steamed lignocellulosic biomass in a second container with a pretreatment liquor at a temperature between about 145° C. and about 165° C. under pressure for 20-120 minutes;
    wherein the pretreatment liquor comprises 6-8 weight % sulfur dioxide, 30-60 weight % ethanol, and 32-64 weight % water (including water from the steamed lignocellulosic biomass), and the ratio of pretreatment liquor to lignocellulosic biomass, based on dry weight of the lignocellulosic biomass, is about 2.5 to 4 kg/kg (including water from the steamed lignocellulosic biomass in the mass of the pretreatment liquor);
    thereby releasing and/or dissolving lignin and hemicellulose from the lignocellulosic biomass into the pretreatment liquor, resulting in a mixture comprising lignin and hemicellulose dissolved in the pretreatment liquor and a solid fraction comprising mainly cellulose from the lignocellulosic biomass, which mixture is referred to as the pretreated material;
    wherein about 10-40% of the lignin from the lignocellulosic biomass is sulfonated to produce lignosulfonic acid (LS), at least 10% of the lignin moieties are ethoxylated, at least about 30% of the sugar moieties of the hemicellulose from the lignocellulosic biomass are hydrolyzed to monosaccharide form, and 20-70% of the sugar moieties of the hemicellulose from the lignocellulosic biomass are converted to ethoxylated sugars;
    (c) releasing pressure from the pretreated material and recovering sulfur dioxide, and optionally ethanol, from gas released from the pretreated material as a result of releasing pressure;
    (d) washing the solid fraction comprising mainly cellulose obtained from the second container with a solution comprising water and ethanol (ranging from 0% to 100% in ethanol concentration), and further washing the solid fraction with water, to provide a washed cellulose stream and a wash filtrate, thereby removing ethanol and dissolved material from the cellulose, wherein the wash filtrate contains the dissolved material, which comprises lignin, ethoxylated lignin, lignosulfonic acid (LS), hemicellulose oligomers, ethoxylated sugars, and monosaccharides;
    (e) recovering ethanol from the wash filtrate, thereby precipitating lignin and ethoxylated lignin fractions, and optionally removing the precipitated lignin fractions;
    (f) heating the material obtained after step (e) at a temperature between 90° C. and 120° C. for 0.5-8 hours to hydrolyze the ethoxylated sugars and hemicellulose oligomers to monosaccharides and to optionally hydrolyze ethoxylated lignin to release ethanol, to provide a composition, referred to as a hemicellulose stream, comprising of lignosulfonic acid and monosaccharides, optionally hydroxylated lignin and lignin, wherein the hydroxylated lignin and lignin may optionally be removed;

(g) optionally adjusting the pH of the washed cellulose stream from step (d) and contacting it with a cellulase, a glucosidase, a hemicellulase, or a combination thereof, to produce glucose, which is referred to as the glucose fraction and release a small amount of other sugars and insoluble lignin; or optionally combining the washed cellulose with the hemicellulose stream from step (f), adjusting the pH of the mixture and contacting it with a cellulase, a glucosidase, a hemicellulase, or a combination thereof, to produce glucose and hemicellulose sugars, and to release a small amount of insoluble lignin;

(h) combining the glucose fraction of step (g) with the hemicellulose stream of step (f) to provide a fermentable composition;

or maintaining the glucose fraction of step (g) and the hemicellulose stream of step (f) separately; and (i) optionally adjusting the pH of the glucose fraction of step (g), the hemicellulose stream of step (f), or the combination thereof, to appropriate pH levels for fermentation, and subjecting the fraction, stream, or combination thereof, to fermentation to produce ethanol;

wherein a high yield of ethoxylated and hydroxylated lignin fractions is defined as at least 65% based on the amount of lignin in the lignocellulosic biomass of step (a), a high yield of lignocellulosic sugars is defined as at least 78% based on the amount of available saccharides in the lignocellulosic biomass, and a high yield of ethanol is defined as at least 43 g per 100 g of monosaccharides present in step (i).

2. The process of claim 1 wherein recovering sulfur dioxide in step (c) comprises:

(i) releasing gaseous vapors from the pretreated material at elevated temperature and/or at a lower pressure, wherein the gaseous vapors released from the pretreated material comprise sulfur dioxide and one or more of water vapor and ethanol vapor;

(ii) condensing at least a portion of the gaseous vapors to provide sulfur dioxide gas and a liquid containing at least one of water and ethanol;

(iii) liquefying sulfur dioxide gas by pressure change and/or temperature reduction of the sulfur dioxide gas, thereby providing liquid sulfur dioxide; and optionally storing the liquid sulfur dioxide; and (iv) introducing the liquid sulfur dioxide to the second container of step (b) or another pretreatment vessel, optionally by pumping.

3. The process of claim 1 where the step (b) pretreatment is performed in a continuous mode.

4. The process of claim 1 where the step (b) pretreatment is performed in a batch mode.

5. The process of claim 1 where the step (g) enzymatic hydrolysis is performed in a continuous mode.

6. The process of claim 1 where the step (g) enzymatic hydrolysis is performed in a batch mode.

7. The process of claim 1 further comprising bleaching the solid fraction that comprises mainly cellulose obtained in step (b), referred to as the washed pulp, to produce bleached cellulose.

8. A process for the production of ethoxylated and hydroxylated lignin fractions, cellulose, lignocellulosic sugars, and ethanol, in high yields, comprising:

(a) contacting lignocellulosic biomass with steam in a first container to provide steamed lignocellulosic biomass;

(b) contacting the steamed lignocellulosic biomass in a second container with a pretreatment liquor at a temperature between 144° C. and 166° C. under pressure for 40-120 minutes;

wherein the pretreatment liquor comprises 7-8 weight % sulfur dioxide, 40-60 weight % ethanol, and 32-54 weight % water (including water from the steamed lignocellulosic biomass), and the ratio of pretreatment liquor to lignocellulosic biomass, based on dry weight of the lignocellulosic biomass, is about 2.5 to about 4 kg/kg (including water from the steamed lignocellulosic biomass in the mass of the pretreatment liquor);

thereby releasing and/or dissolving lignin and hemicellulose from the lignocellulosic biomass into the pretreatment liquor, resulting in a mixture comprising lignin and hemicellulose dissolved in the pretreatment liquor and a solid fraction comprising cellulose from the lignocellulosic biomass, which mixture is referred to as the pretreated material;

wherein about 10-40% of the lignin from the lignocellulosic biomass is sulfonated to produce lignosulfonic acid (LS), at least 10% of the lignin moieties are ethoxylated, at least about 30% of the sugar moieties of the hemicellulose from the lignocellulosic biomass are hydrolyzed to monosaccharide form, 30-80% of the sugar moieties of the hemicellulose from the lignocellulosic biomass are converted to ethoxylated sugars, the cellulosic pulp yield is at least 40%, the acetyl groups in the solid fraction comprising cellulose is less than 0.1%, and the solid fraction comprising cellulose comprises less than 2.1% lignin;

(c) releasing pressure from the pretreated material and recovering sulfur dioxide and ethanol from gas released from the pretreated material as a result of releasing pressure;

(d) washing the solid fraction comprising cellulose obtained from the second container with a solution comprising water and ethanol (ranging from 40% to 60% in ethanol concentration), and further washing the solid fraction with water, to provide washed cellulose and a wash filtrate, thereby removing ethanol and dissolved material from the cellulose, wherein the wash filtrate contains the dissolved material, which comprises lignin, ethoxylated lignin, lignosulfonic acid (LS), hemicellulose oligomers, ethoxylated sugars, and monosaccharides;

(e) recovering ethanol from the wash filtrate, thereby precipitating lignin and ethoxylated lignin fractions;

(f) heating the material obtained after step (e) at a temperature between 100° C. and 125° C. for 0.5-2 hours to hydrolyze the ethoxylated sugars and hemicellulose oligomers to monosaccharides and to hydrolyze ethoxylated lignin to release ethanol, to provide a composition, referred to as a hemicellulose stream, comprising of lignosulfonic acid and monosaccharides, and hydroxylated lignin and lignin;

(g) adjusting the pH of the washed cellulose stream from step (d) to a pH between 4.8 and 5.8 and contacting it with a combination of cellulases, glucosidases, and hemicellulases at a temperature of about 50° C. to about 56° C. to produce glucose, which is referred to as a glucose fraction;

(h) combining the glucose fraction of step (g) with the hemicellulose stream of step (f) to provide a fermentable composition, wherein the combined glucose fraction and hemicellulose stream comprises less than 0.9% of furfural, hydroxymethylfurfural, and levulinic acid combined, and the combined glucose fraction and hemicellulose stream comprises a total saccharide recovery from the lignocellulosic biomass of at least 96%; and (i) adjusting the pH of the fermentable composition of step (h) to a pH between 5.0 and 6.0, and subjecting the pH-adjusted fermentable composition to fermentation by yeast at a temperature between 30° C. and 34° C. to produce ethanol;

wherein a high yield of ethoxylated and hydroxylated lignin fractions is defined as at least 76% based on the amount of lignin in the lignocellulosic biomass of step (a), a high yield of lignocellulosic sugars is defined as at least 87% based on the amount of available saccharides in the lignocellulosic biomass, and a high yield of ethanol is defined as at least 43 g per 100 g of monosaccharides present in step (i).

9. The process of claim 8 wherein the process produces at least 74% non-condensed reactive lignin, based on amount of lignin in the lignocellulosic biomass used in the process.

10. A process for the production of ethoxylated and hydroxylated lignin fractions, cellulose, lignocellulosic sugars, and ethanol, in high yields, consisting essentially of:

(a) contacting softwood biomass with steam in a first container to provide steamed lignocellulosic biomass;

(b) contacting the steamed lignocellulosic biomass in a second container with a pretreatment liquor at a temperature of about 155° C. to about 160° C. under pressure for 45-75 minutes;

wherein the pretreatment liquor consists essentially of 7-8 weight % sulfur dioxide, 40-60 weight % ethanol, and 32-54 weight % water (including water from the steamed lignocellulosic biomass), and the ratio of pretreatment liquor to lignocellulosic biomass, based on dry weight of the lignocellulosic biomass, is about 2.5 to about 4 kg/kg (including water from the steamed lignocellulosic biomass in the mass of the pretreatment liquor);

thereby releasing and/or dissolving lignin and hemicellulose from the lignocellulosic biomass into the pretreatment liquor, resulting in a mixture comprising lignin and hemicellulose dissolved in the pretreatment liquor and a solid fraction comprising cellulose from the lignocellulosic biomass, which mixture is referred to as the pretreated material;

wherein about 10-40% of the lignin from the lignocellulosic biomass is sulfonated to produce lignosulfonic acid (LS), at least 10% of the lignin moieties are ethoxylated, at least about 30% of the sugar moieties of the hemicellulose from the lignocellulosic biomass are hydrolyzed to monosaccharide form, 30-80% of the sugar moieties of the hemicellulose from the lignocellulosic biomass are converted to ethoxylated sugars, the cellulosic pulp yield is at least 40%, the acetyl groups in the solid fraction comprising cellulose is less than 0.1%, and the solid fraction comprising cellulose comprises less than 2.1% lignin;

(c) releasing pressure from the pretreated material and recovering sulfur dioxide and ethanol from gas released from the pretreated material as a result of releasing pressure;

(d) washing the solid fraction comprising cellulose obtained from the second container with a solution comprising water and ethanol (ranging from 40% to 60% in ethanol concentration), and further washing the solid fraction with water, to provide washed cellulose and a wash filtrate, thereby removing ethanol and dissolved material from the cellulose, wherein the wash filtrate contains the dissolved material, which comprises lignin, ethoxylated lignin, lignosulfonic acid (LS), hemicellulose oligomers, ethoxylated sugars, and monosaccharides;

(e) recovering ethanol from the wash filtrate, thereby precipitating lignin and ethoxylated lignin fractions;

(f) heating the material obtained after step (e) at a temperature between 100° C. and 125° C. for 0.5-2 hours to hydrolyze the ethoxylated sugars and hemicellulose oligomers to monosaccharides and to hydrolyze ethoxylated lignin to release ethanol, to provide a composition, referred to as a hemicellulose stream, comprising of lignosulfonic acid and monosaccharides, and hydroxylated lignin and lignin;

(g) adjusting the pH of the washed cellulose stream from step (d) to a pH between 4.8 and 5.8 and contacting it with a combination of cellulases, glucosidases, and hemicellulases at a temperature of about 50° C. to about 56° C. to produce glucose, which is referred to as a glucose fraction;

(h) combining the glucose fraction of step (g) with the hemicellulose stream of step (f) to provide a fermentable composition, wherein the combined glucose fraction and hemicellulose stream comprises less than 0.9% of furfural, hydroxymethylfurfural, and levulinic acid combined, and the combined glucose fraction and hemicellulose stream comprises a total saccharide recovery from the lignocellulosic biomass of at least 96%; and (i) adjusting the pH of the fermentable composition of step (h) to a pH between 5.0 and 6.0, and subjecting the pH-adjusted fermentable composition to fermentation by yeast at a temperature between 30° C. and 34° C. to produce ethanol;

wherein a high yield of ethoxylated and hydroxylated lignin fractions is defined as at least 76% based on the amount of lignin in the lignocellulosic biomass of step (a), a high yield of lignocellulosic sugars is defined as at least 87% based on the amount of available saccharides in the lignocellulosic biomass, and a high yield of ethanol is defined as at least 43 g per 100 g of monosaccharides present in step (i).

* * * * *